(12) United States Patent
Hennessey et al.

(10) Patent No.: US 10,182,720 B2
(45) Date of Patent: Jan. 22, 2019

(54) SYSTEM AND METHOD FOR INTERACTING WITH AND ANALYZING MEDIA ON A DISPLAY USING EYE GAZE TRACKING

(71) Applicant: TandemLaunch Technologies Inc., Westmount (CA)

(72) Inventors: Craig A. Hennessey, Westmount (CA); Jacob Fiset, Berlioz (CA)

(73) Assignee: Mirametrix Inc., Montreal (CA)

( * ) Notice: Subject to any disclaimer, the term of this patent is extended or adjusted under 35 U.S.C. 154(b) by 511 days.

(21) Appl. No.: 13/870,888

(22) Filed: Apr. 25, 2013

(65) Prior Publication Data

US 2013/0235347 A1    Sep. 12, 2013

Related U.S. Application Data

(63) Continuation of application No. PCT/CA2011/001213, filed on Nov. 4, 2011.

(60) Provisional application No. 61/413,964, filed on Nov. 15, 2010.

(51) Int. Cl.
    *A61B 3/14*    (2006.01)
    *A61B 3/113*   (2006.01)
    *G06F 3/01*    (2006.01)
    *G06K 9/00*    (2006.01)

(52) U.S. Cl.
    CPC .............. *A61B 3/113* (2013.01); *G06F 3/013* (2013.01); *G06K 9/00604* (2013.01); *G06K 9/00845* (2013.01)

(58) Field of Classification Search
    CPC .............. G02F 1/167; G02F 1/133516; G02F 2001/133354; G02F 1/17; H01J 9/24; G06F 3/013; G06F 3/038; G06F 2203/0381; G06F 3/1446; G06F 17/30017; G06F 1/3231; G06F 3/147; G06T 2207/30041; G06T 11/00; G06T 15/00; G06T 2219/2021;
    (Continued)

(56) References Cited

U.S. PATENT DOCUMENTS 4,973,149 A * 11/1990 Hutchinson ............ A61B 3/113
                                                       351/210
5,886,683 A *  3/1999 Tognazzini ............. G06F 3/013
                                                       345/156
(Continued)

OTHER PUBLICATIONS

Linco, R.; Search Report from corresponding PCT Application No. PCT/CA2011/001213; search completed Feb. 8, 2012.

*Primary Examiner* — Mustak Choudhury
(74) *Attorney, Agent, or Firm* — Brett J. Slaney; Blake, Cassels & Graydon LLP

(57) ABSTRACT

A system and method are provided that use eye gaze as a pointing or selection tool, which enables hands-free operation of a display such as a television. wherein the use of eye gaze as an input can also lead to easier and faster interactions when compared to traditional remote controls. A system and method are also provided that use eye tracking on displays such as televisions to determine what content was viewed and, by association, what content was of most interest to the user. Systems and methods are also described that enable interaction with elements displayed in an augmented reality environment using gaze tracking and for controlling gaze tracking on a portable electronic device.

45 Claims, 17 Drawing Sheets

(58) Field of Classification Search
CPC ... G06T 7/20; G06K 9/00604; G06K 9/00597
USPC ........ 351/205–210, 222, 246; 345/156, 173;
382/103, 116, 117, 299; 705/14.66
See application file for complete search history.

(56) References Cited

U.S. PATENT DOCUMENTS

| | | | |
|---|---|---|---|
| 6,204,828 B1* | 3/2001 | Amir | G06F 3/013 |
| | | | 345/156 |
| 6,243,076 B1 | 6/2001 | Hatfield | |
| 6,351,273 B1 | 2/2002 | Lemelson et al. | |
| 7,068,813 B2 | 6/2006 | Lin | |
| 7,561,143 B1 | 7/2009 | Milekic | |
| 8,494,215 B2* | 7/2013 | Kimchi | G06F 3/013 |
| | | | 382/103 |
| 2002/0105482 A1* | 8/2002 | Lemelson | G06F 3/013 |
| | | | 345/7 |
| 2005/0047629 A1 | 3/2005 | Farrell et al. | |
| 2008/0065468 A1* | 3/2008 | Berg | G06Q 30/0203 |
| | | | 705/7.32 |
| 2009/0322671 A1 | 12/2009 | Scott et al. | |
| 2010/0156781 A1 | 6/2010 | Fahn | |
| 2010/0161426 A1 | 6/2010 | Dhawan et al. | |
| 2010/0162320 A1 | 6/2010 | Bennett et al. | |
| 2010/0223639 A1 | 6/2010 | Reichardt et al. | |
| 2010/0188334 A1 | 7/2010 | Yamamoto et al. | |
| 2010/0194977 A1 | 8/2010 | Sloo et al. | |
| 2010/0214495 A1 | 8/2010 | Lowe | |
| 2010/0226535 A1* | 9/2010 | Kimchi | G06F 3/013 |
| | | | 382/103 |

* cited by examiner

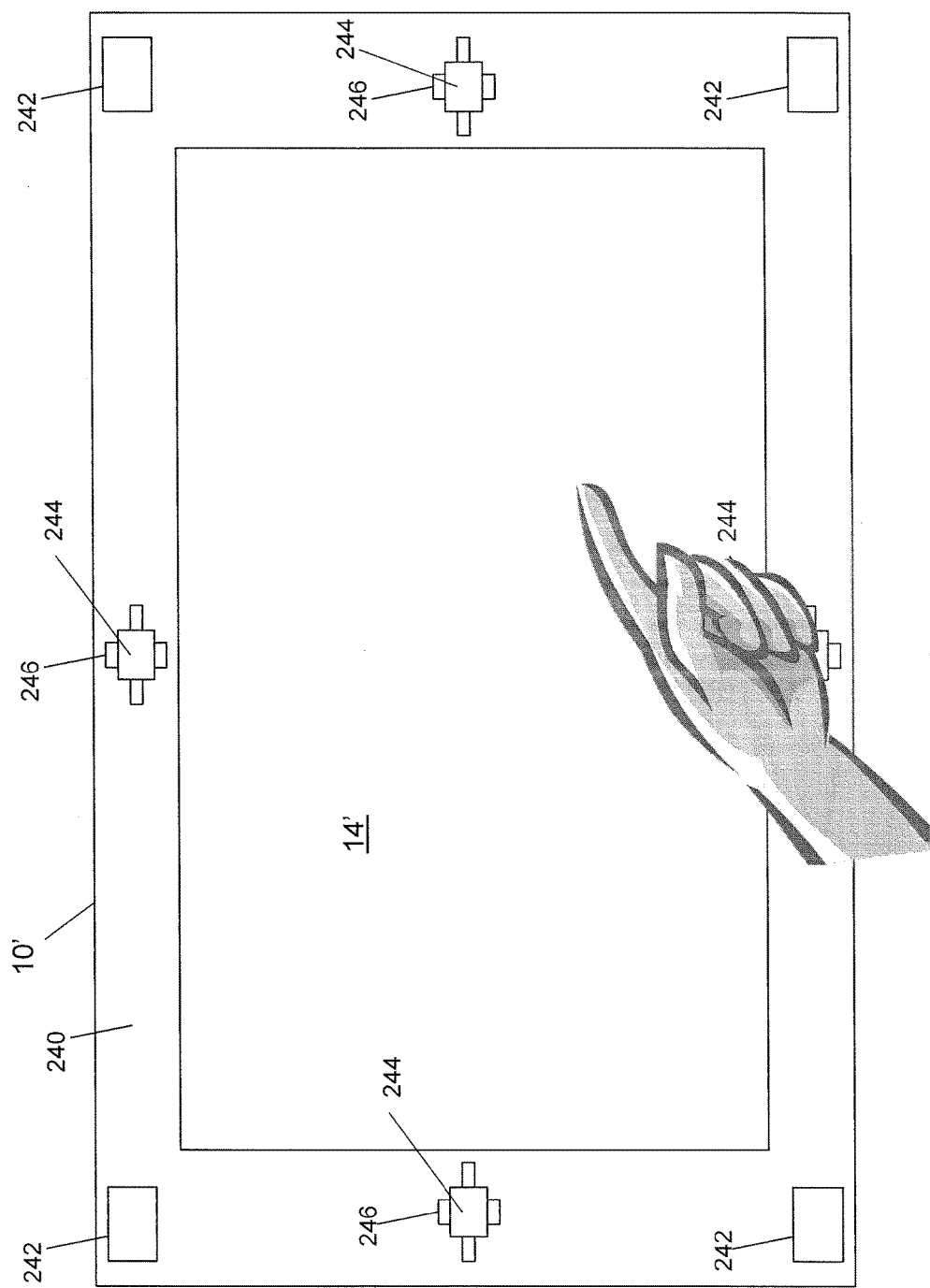

SYSTEM AND METHOD FOR INTERACTING WITH AND ANALYZING MEDIA ON A DISPLAY USING EYE GAZE TRACKING

CROSS-REFERENCE TO RELATED APPLICATIONS

This application is a continuation of International PCT Application No. PCT/CA2011/001213 filed on Nov. 4, 2011 which claims priority from U.S. Provisional Application No. 61/413,964 filed on Nov. 15, 2010, the contents of which are both incorporated herein by reference.

TECHNICAL FIELD

The following relates to systems and methods for interacting with and/or analyzing media on a display using eye gaze tracking.

DESCRIPTION OF THE RELATED ART

Eye-tracking systems provide a powerful tool for monitoring human-computer interactions. For example, where a viewer is looking can often be tied to what the viewer is interested in, or what caught the user's attention. With the rapid advance in computing power, and equivalent decrease in cost, there is now a convergence of computers and all forms of displays. With this convergence, it is now commercially possible for eye tracking systems to be integrated with, or used in addition to, televisions or other consumer level displays such as projector screens, mobile devices, augmented reality, etc., and in real-world environments such as the home, office, etc., rather than just at dedicated research facilities.

SUMMARY

In one aspect, there is provided a method of interacting with media content using gaze information, the method comprising: obtaining gaze information for at least one subject viewing media content on a display in an environment; associating the gaze information with a portion of the media content being displayed; and interacting with the media content being displayed according to the associated portion.

In another aspect, there is provided a method of tracking gaze information, the method comprising: obtaining a first image of an environment using a first imaging device; identifying a subject in the first image; orienting a second imaging device towards a position associated with the identified subject; obtaining a second image of the subject; and utilizing the second image in tracking gaze information for the subject.

In yet another aspect, there is provided a method of enabling interaction with elements displayed in an augmented reality (AR) environment, the method comprising: overlaying at least one element on a viewing area in the AR environment; obtaining an image of a subject in the AR environment viewing the viewing area; determining gaze information from the image; associating the gaze information with the at least one element overlaid on the viewing area; and performing an action according to the gaze information.

In yet another aspect, there is provided a method of controlling a gaze tracking system on a portable electronic device, the gaze tracking system for enabling interaction with a display of the portable electronic device, the method comprising: detecting a tilt angle with respect to the portable electronic device; orienting at least one of a plurality of gaze tracking cameras on the device according to the tilt angle; and selecting at least one camera obtaining an image not being obscured.

In yet another aspect, there is provided a method of controlling a gaze tracking system on a portable electronic device, the gaze tracking system for enabling interaction with a display of the portable electronic device, the method comprising: obtaining an image from each of a plurality of gaze tracking cameras on the device; selecting the image obtained by the camera positioned lowest on the device; and utilizing the image obtained from the lowest camera in determining gaze information for a user of the device.

In yet another aspect, there is provided a method of controlling a gaze tracking system on a portable electronic device, the gaze tracking system for enabling interaction with a display of the portable electronic device, the method comprising: powering lights associated with a plurality of gaze tracking camera on the device only when an associated camera shutter is open.

In yet another aspect, there is provided a method of controlling a gaze tracking system on a portable electronic device, the gaze tracking system for enabling interaction with a display of the portable electronic device, the method comprising: using a hardware region of interest with a gaze tracking camera on the device, wherein only a portion of a sensor in the camera that is imaging eyes is transmitted to a central processing unit of the device.

In further aspects, computer readable media storing computer readable instructions, and systems operable for performing the above methods are also provided.

BRIEF DESCRIPTION OF THE DRAWINGS

Embodiments will now be described by way of example only with reference to the appended drawings wherein:

FIG. 16 is a plan view of the display of FIG. 15 with an obstruction over an eye tracking camera.

DETAILED DESCRIPTION

Figure 1:
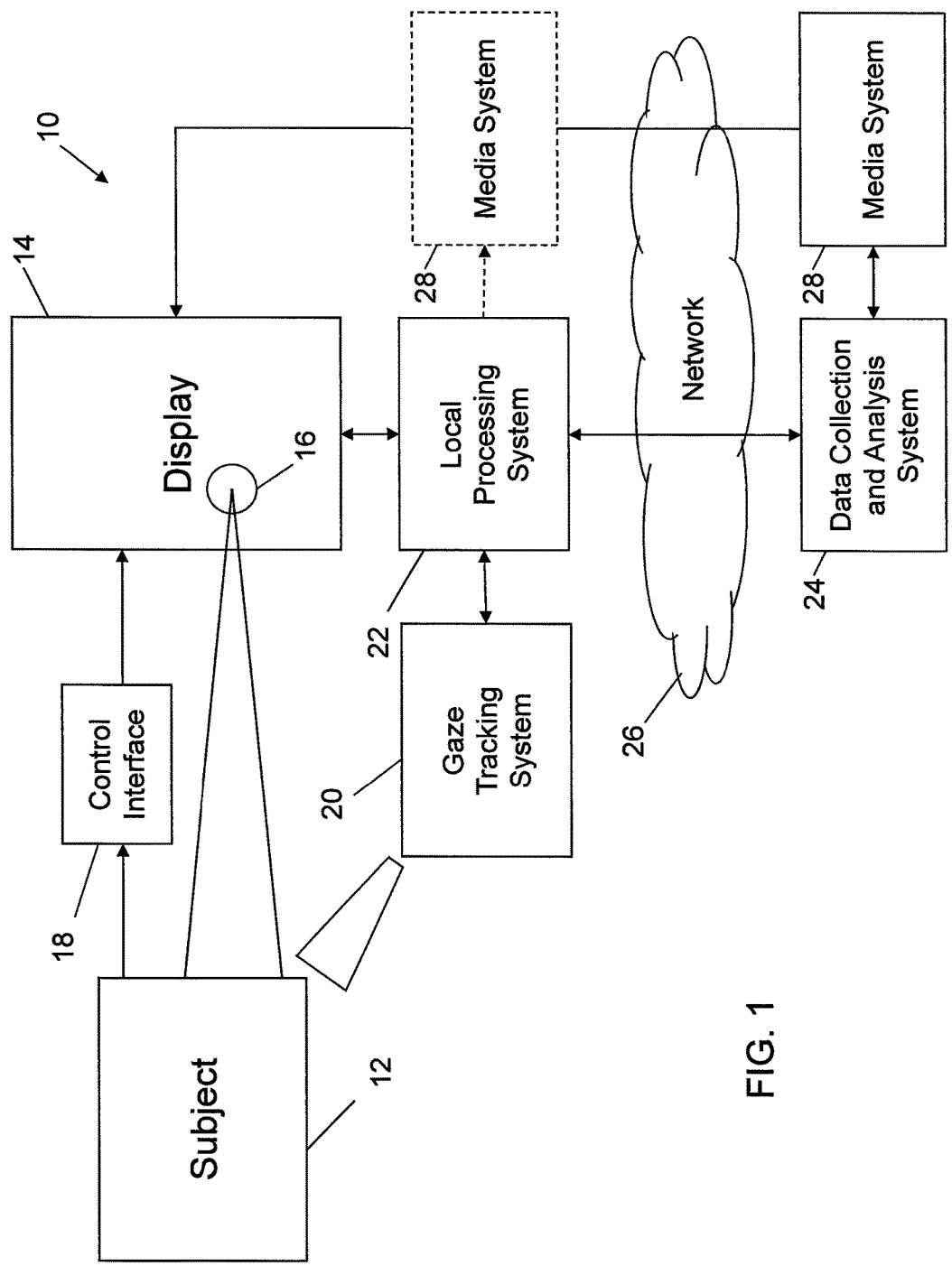
FIG. 1 is a block diagram showing an example of a subject viewing and/or interacting with a display and an eye gaze tracking system for tracking the subject to detect interactions with content on the display and to analyze the content associated with eye gaze.

It will be appreciated that for simplicity and clarity of illustration, where considered appropriate, reference numerals may be repeated among the figures to indicate corresponding or analogous elements. In addition, numerous specific details are set forth in order to provide a thorough understanding of the examples described herein. However, it will be understood by those of ordinary skill in the art that the examples described herein may be practiced without these specific details. In other instances, well-known methods, procedures and components have not been described in detail so as not to obscure the examples described herein. Also, the description is not to be considered as limiting the scope of the examples described herein.

It will also be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

It has been recognized that eye gaze can be used as a pointing or selection tool, which enables hands-free operation of a display such as a television. In this way, a subject viewing the display may simply look at on-screen elements to control the system. For example, by looking at a volume-up button, the system can react by increasing the volume for audio associated with the content being displayed. Activation of control elements can also be made using dwell time, blinks, or, if a remote control device is available, a simple push button selector. Using eye gaze for controlling the display provides a convenient, intuitive, and enjoyable way for enabling a subject to operate displays such as televisions. Moreover, the use of eye gaze as an input can also lead to easier and faster interactions when compared to traditional remote controls.

It can also been recognized that eye tracking on displays such as televisions can be used to determine what content was viewed and, by association, what content was of most interest to the user. Alternatively, knowing what content was not viewed also provides useful information on what was not of interest, or did not catch the attention of the subject.

Viewer behavior tracking for television is also a known market research tool for establishing the viewing habits of a population or demographic. It has been found that the addition of eye gaze tracking provides information regarding which elements of the media content the viewer actually viewed, and not just what channel or program was on the screen. Eye gaze data can be collected, aggregated, and used in further market research for better understanding the viewer's habits. Additionally, eye gaze information may be useful in providing subjects with a stream of programming specifically tailored to their interests based on their viewing patterns. For example, by analyzing what catches the attention of a particular demographic, content can be tailored accordingly.

The following provides a system and method that is operable to utilize eye gaze tracking to enable interactions with content being displayed and to analyze or have analyzed, how the subject interacts with the media content, e.g., what is viewed, for how long, etc.

Turning now to FIG. 1, an environment 10 is shown with which a subject 12 views or interacts with a display 14 in or provided by the environment 10. The environment 10 may be associated with a physical location such as an office, movie theatre, home theatre, etc.; or may represent components of one or more devices such as a television, smart phone, personal computer (PC), gaming console, tablet computer, etc. The display 14 may therefore be provided by or associated with any device capable of displaying media content to a subject (e.g., user, viewer, etc.). For example, the display 14 may represent a screen for a television (TV), computer monitor, mobile device, augmented or virtual-reality display, etc. and may provide a two dimensional (2D) or a three dimensional (3D) output.

In the example shown in FIG. 1, the subject 12 when viewing the display 14 has a direction of gaze, also known as a line of sight, which is the vector that is formed from the eye of the subject to a point on a object of interest on the display 14. The point of gaze (POG) 16 is the intersection point of the line of sight with the object of interest. The object of interest in this example corresponds to a virtual object displayed on the display 14. For 2D displays 14, the POG 16 lies on the surface of the display 14. For 3D displays 14, the POG 16 targets objects similarly to real-world objects, using the vergence of the eyes of the subject, or intersection of the line of sight from both the left and right eyes of the subject. The movement of the eyes can be classified into a number of different behaviors, however of most interest when tracking the POG 16, are typically fixations and saccades. A fixation is the relatively stable positioning of the eye, which occurs when the user is observing something of interest. A saccade is a large jump in eye position which occurs when the eye reorients itself to look towards a new object. Fixation filtering is a technique which can be used to analyze recorded gaze data and detects fixations and saccades. The movement of the subject's eyes and gaze information, POG 16 and other gaze-related data is tracked by a gaze tracking system 20.

Media content is provided on the display 14 for the subject 12 using a media system 22. In the example shown in FIG. 1 it is assumed that the media content being consumed is fed to or obtained by the display 14 from a remotely located media system 28, e.g., a network service such as a television channel. As shown in FIG. 1, it can be appreciated that the media system 28 may also or instead reside locally with respect to the display 14, e.g., media played from a disc or stored media file. In addition to displaying media content using the display 14, the environment may be operable to provide a control interface 18 such as a handheld remote control that includes one or more input mechanisms with which the subject 12 may interact with the display 14 and any system controlling the display 14. For example, the control interface 18 may be provided by a standard television remote control which converts tactile inputs or button presses to infrared or other signals to control the display 14.

A gaze tracking system 20 captures eye gaze information associated with the subject 12. It can be appreciated that in the event that there are multiple subjects 12 viewing the same display 14, the gaze tracking system 20 may track the multiple subjects 12 or multiple gaze tracking systems 20 may be used, one being assigned to each subject 12. The eye gaze information is provided by the gaze tracking system 20 to a local processing system 22 to collect eye gaze data for further processing, e.g., to perform local processing and/or analysis if applicable, or to provide the eye gaze information to a remote data collection and analysis system 24. It can be appreciated that the local processing system 22 may also be remote to the gaze tracking system 20 and environment 10. Similarly, the data collection and analysis operations discussed below may also be performed locally. As such, the configuration shown in FIG. 1 is illustrative only and may be adapted for different applications, e.g., according to the environment 10, the device including the display 14, etc.

The local processing system 22, in the example shown in FIG. 1, may be a separate computer, or a computer or processor integrated with the display 14. The gaze data being collected and processed may include where the user is looking on the display 14 for both the left and right eyes, the position of the subject's head and eyes with respect to the display 14, the dilation of the subject's pupils, and other parameters of interest. The local processing system 22 may also use the eye gaze data for navigating menus on the display 14, examples of which will be described below. In applications wherein the local processing system 22 is used to control the content on the display 14, the local processing system 22 may also provide directed content (e.g., by controlling the media system 28 or the display 14 directly), based on the subject's gaze pattern. As discussed above, the displayed content may also be delivered from an external media system 28 or other source. For example, the environment 10 may receive a media feed using a satellite dish, cable connection, the Internet, or other content delivery medium.

The data collected at the data collection and analysis system 24 can be analyzed based on, for example, the demographics of the viewers, statistics calculated for content elements (e.g., a particular product or brand), etc. Statistics may include time to first view, total time viewed, number of repeated views, etc. Behavioral data such as pupil dilation may also be used to determine the emotional impact of viewing a product brand or other content of interest. Analyses performed at the data collection and analysis system 24 may be used for market research analysis, but may also be used to customize the content being fed to the display 14 based on viewing behaviors, e.g., by controlling or instructing the media system 28. For example, if a shampoo bottle product placement has been shown in a television sitcom program, and a large number of female viewers in the age range of 25-35 years old viewed the shampoo bottle, the following commercial break may contain an advertisement for that particular brand and type of shampoo.

Figure 2:
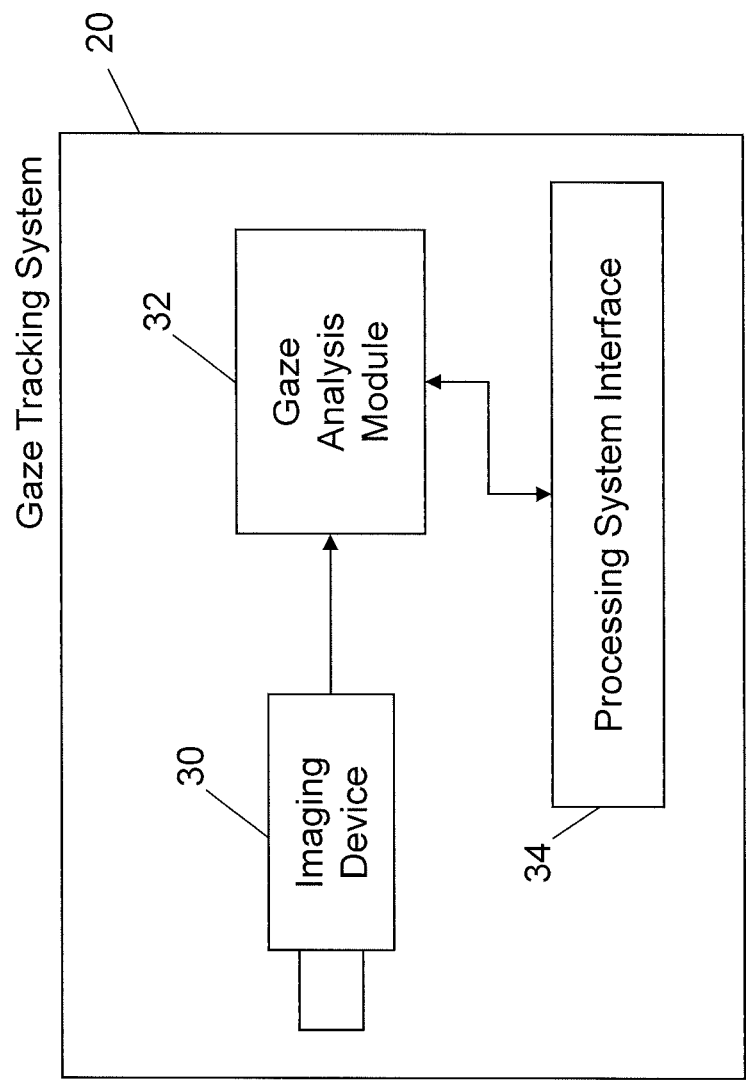
FIG. 2 is a block diagram of an example configuration for the gaze tracking system of FIG. 1.

An example of a configuration for the gaze tracking system 20 is shown in FIG. 2. The gaze tracking system 20 in this example includes an imaging device 30 for tracking the motion of the eyes of the subject 12; a gaze analysis module 32 for performing eye-tracking using data acquired by the imaging device 30; and a processing system interface 34 for interfacing with, obtaining data from, and providing data to, the local processing system 22. The gaze tracking system 20 may incorporate various types of eye-tracking techniques and equipment. An example of an eye-tracking system can be found in U.S. Pat. No. 4,950,069 to Hutchinson and entitled "Eye Movement Detector with Improved Calibration and Speed". It can be appreciated that any commercially available or custom generated eye-tracking or gaze-tracking system, module or component may be used. An eye tracker is used to track the movement of the eye, the direction of gaze, and ultimately the POG 16 of a subject 12. A variety of techniques are available for tracking eye movements, such as measuring signals from the muscles around the eyes, however the most common technique uses the imaging device 30 to capture images of the eyes and process the images to determine the gaze information.

Figure 3:
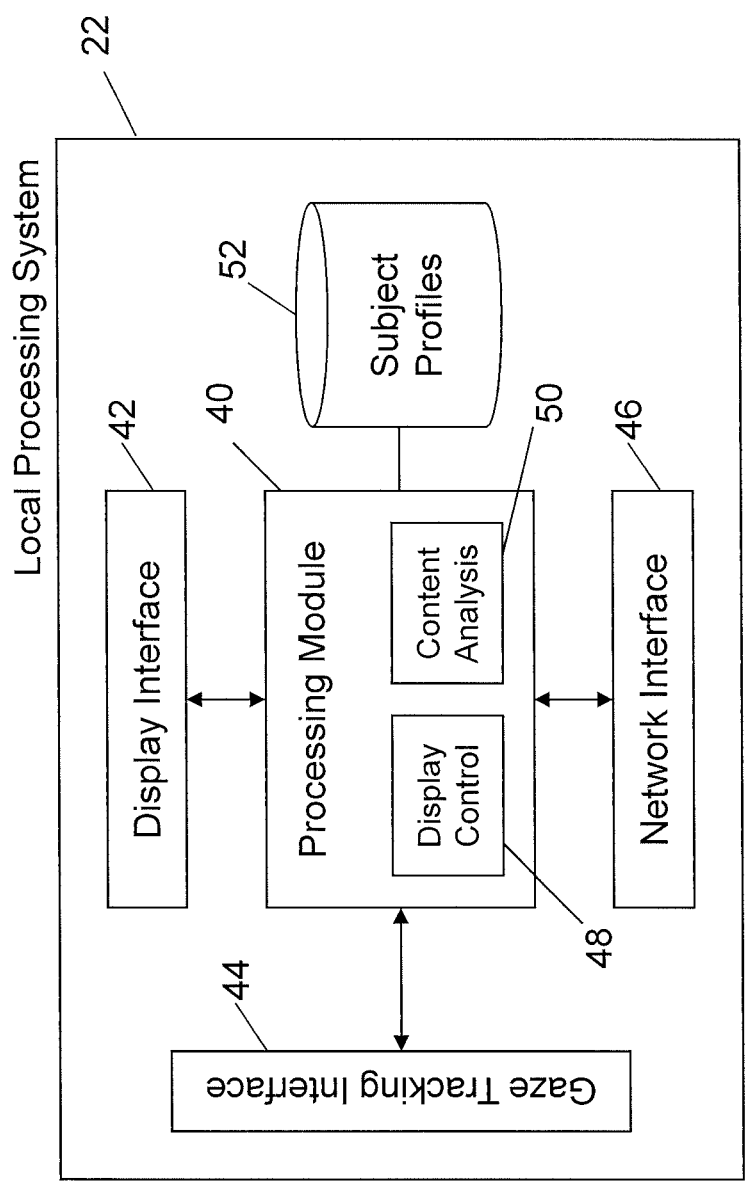
FIG. 3 is a block diagram of an example configuration for the local processing system of FIG. 1.

An example of a configuration for the local processing system 22 is shown in FIG. 3. The local processing system 22 in this example includes a processing module 40 for collecting gaze data from the gaze tracking system 20 via a gaze tracking interface 44 and for performing any local processing, analysis, or control of media content being viewed. The local processing system 22 also include a display interface 42 for providing data to or receiving data from the display 14. For example, the local processing system 22 may be operable to display control elements on the display 14 and track the subject's gaze with respect to such control elements as will be explained in greater detail below. The local processing system 22 also includes a network interface 46 (e.g., Wi-Fi connection, Ethernet connection, etc.) to enable the processing module 40 to provide collected gaze data and/or locally processed gaze data and other data and information to the data collection and analysis system 24 via the network 26.

As noted above, the gaze tracking system 20 may be operable to track multiple subjects 12 and it can be appreciated that this can be done at the same time or in series (i.e. different viewers at different times). Moreover, the gaze tracking system 20 shown in FIGS. 1 and 2 may include multiple gaze tracking sub-systems (not shown) or otherwise be capable of tracking multiple subjects at the same time. As such, the processing module 40 may include or otherwise have access to a subject profiles database 52 storing information related to expected subjects 12. For example, the subject profiles may include information for identifying which subject 12 is currently viewing the display 14 and any available information associated with that subject 12 such as demographic data. It can be appreciated that the gaze tracking system 20 may also include a subject profiles database 52 or be given access to subject profiles by the local processing system 22.

In addition to collecting or receiving gaze data from the gaze tracking system 20, the processing module 40 may include sub-modules or program instructions for providing display control 48 and content analysis 50 components. For example, the display control component 48 could be initiated to perform an action according to a detected selection of a control element displayed on the display 14. In another example, the processing module 40 may use the content analysis component 50 to perform local analyses that link the eye gaze data to what content is being displayed by the media system 28 or to pre-process data that is to be sent to the data collection and analysis system 24 over the network 26.

Figure 4:
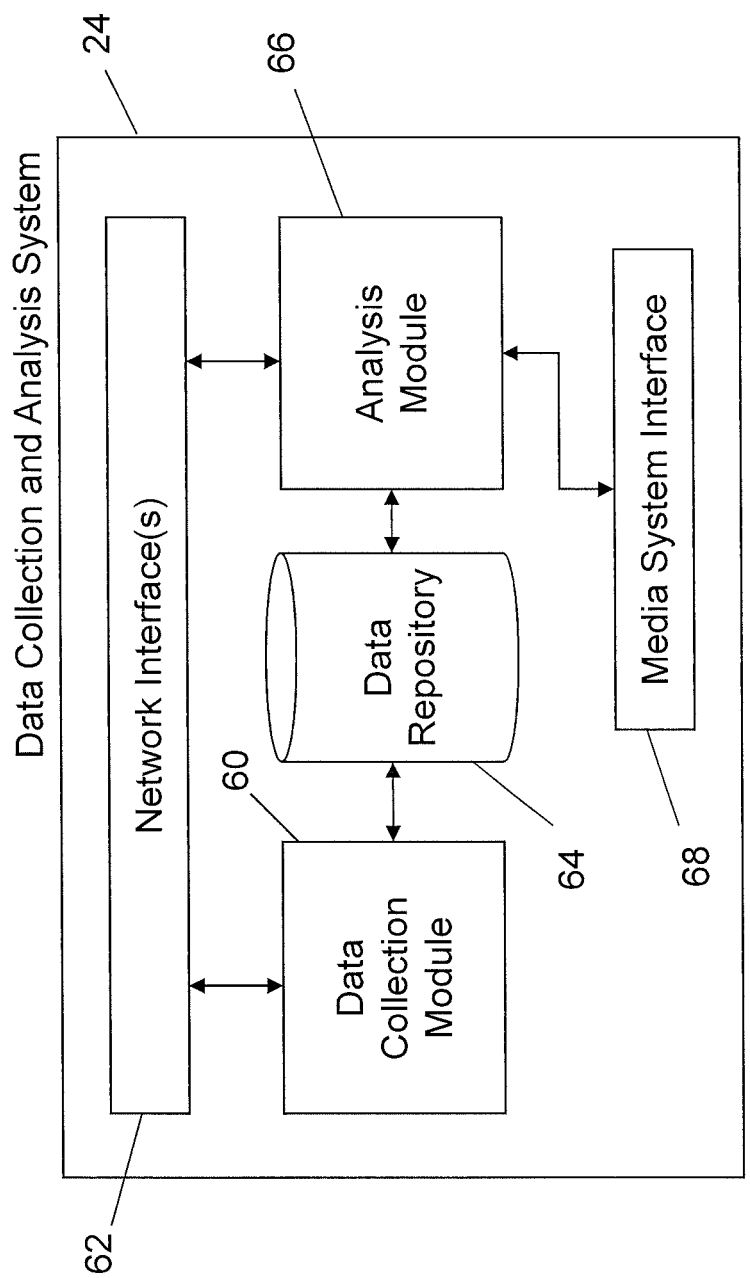
FIG. 4 is a block diagram of an example configuration for the data collection and analysis system of FIG. 1.

An example of a configuration for the data collection and analysis system 24 is shown in FIG. 4. The data collection and analysis system 24 in this example includes one or more network interfaces 62 for enabling a data collection module 60 to receive data from the local processing system 22, and to enable an analysis module 66 to provide data to the local processing system 22, the media system 28 (if network accessible), or the display 14 directly. The data collection module 60 in this example is configured to obtain data and store such data in a data repository 64. The data repository 64 is accessible to the analysis module 66 for using the data in performing analyses. The data collection and analysis system 24 also includes a media system interface 68 to enable the results of gaze and content analyses to be provided to the media system 28, e.g., if the data collection and analysis system 24 are communicable with each other locally rather than over the network 26.

Figure 5:
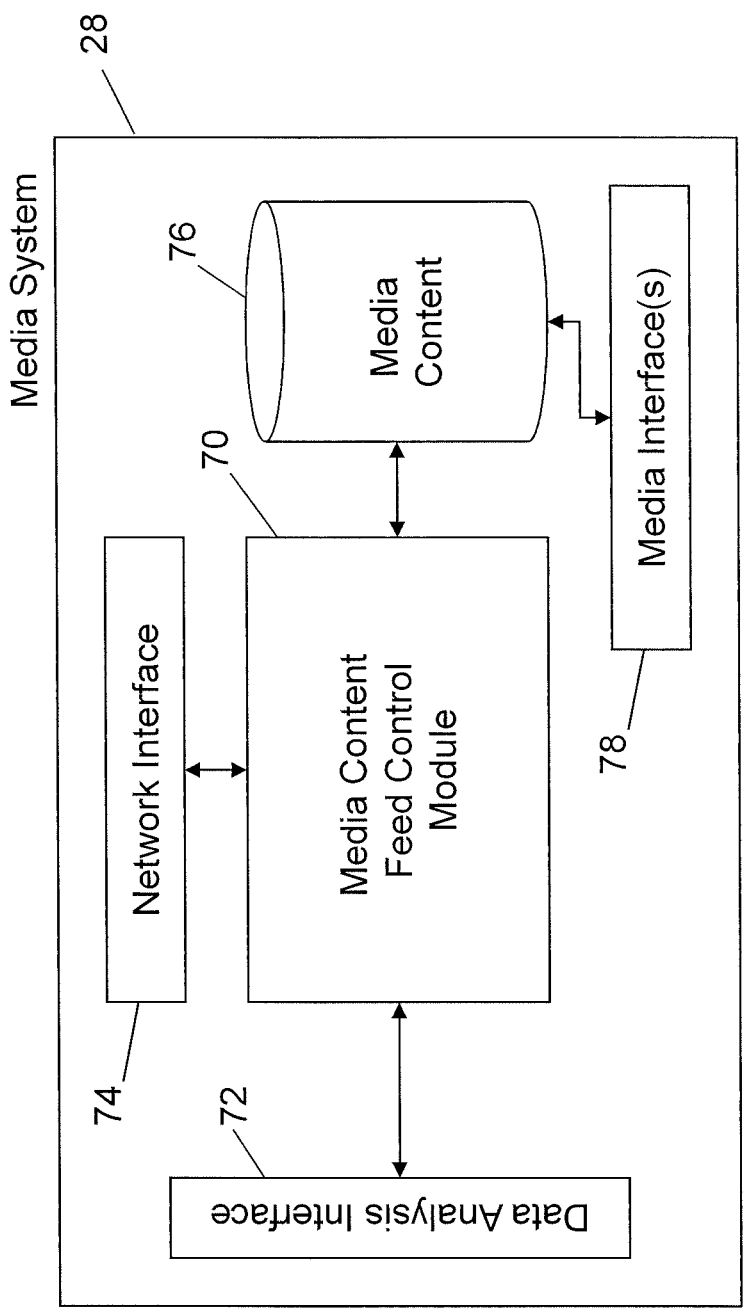
FIG. 5 is a block diagram of an example configuration for the media system of FIG. 1.

An example of a configuration for the media system 28 is shown in FIG. 5. The media system 28 in this example includes a media content feed control module 70, which may represent any component, module, device, or program instructions for providing media content to the display 14. For example, the media content feed control module 70 may be a media player, a content server, a network service, physical medium, etc. In examples where the media system 28 is remote with respect to the environment 10, a network interface 74 may be used to deliver media content over the network to the display 14. It can be appreciated that although not shown in FIG. 5, in example where the media system 28 is locally provided in the environment 10, the media system 28 may include a display interface. The media system 28 also includes a data analysis interface 72 for receiving, for example, analyses results data, from the data collection and analysis system 24. Media content may be stored in a media content database 76. The media content database 76 may also represent or be replaced with a physical medium, media file, streaming media component, etc. in various configurations for the media system 28 and thus it can be appreciated that the configuration shown in FIG. 5 is purely illustrative. One or more media interfaces 78 may also be included to enable media content to be loaded or stored onto the media content database 76. For example, the media interfaces 78 may include media ports (USB, SD, etc.), an Ethernet connection, a Wi-Fi connection, etc.

Figure 6:
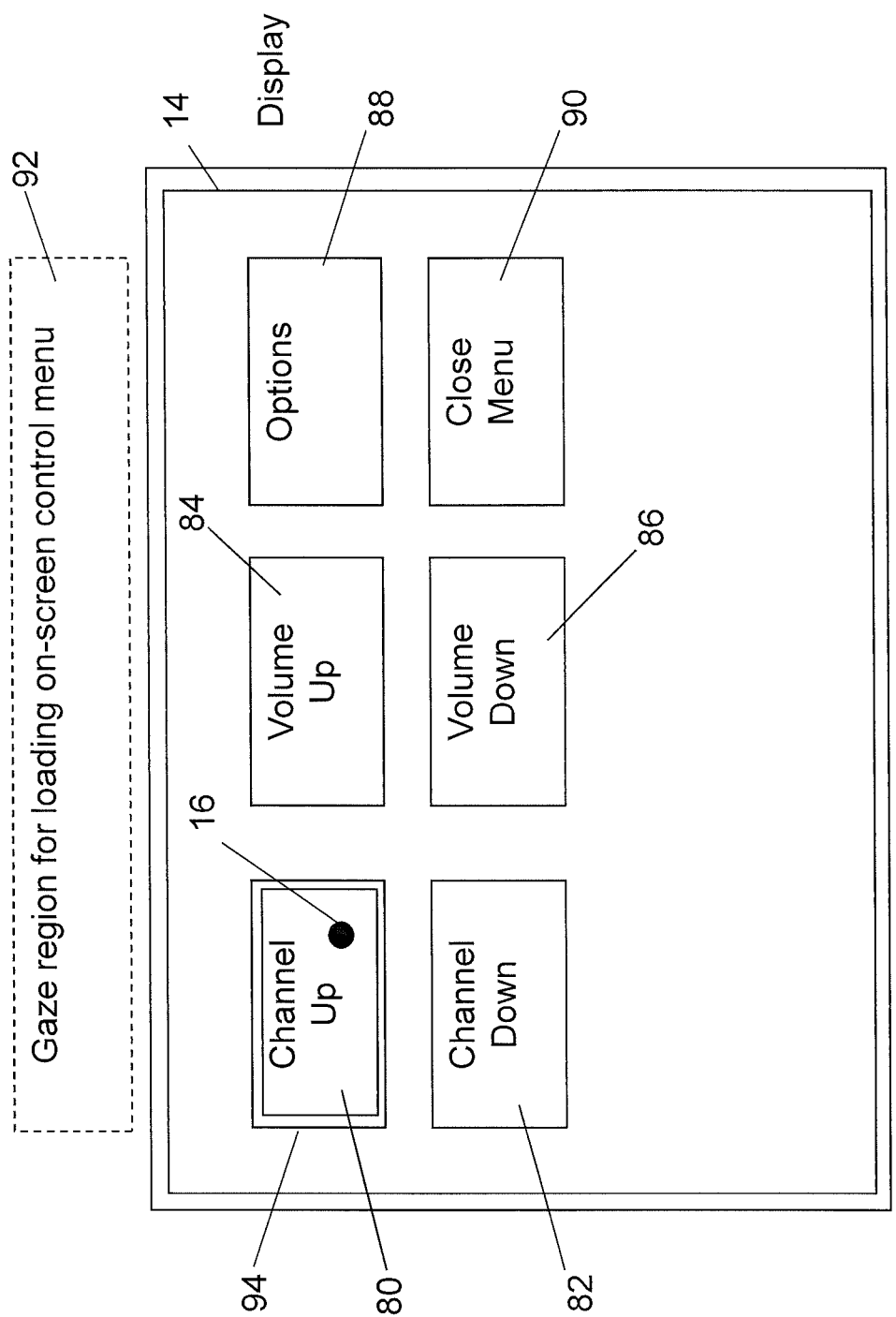
FIG. 6 is an example of a screen shot displaying control elements.

FIG. 6 illustrates an example of a display 14 that is capable of being gaze controlled. In the example shown in FIG. 6, various control elements are displayed on the display 14, including channel up 80, channel down 82, volume up 84, volume down 86, other menu options 88 (e.g., calibration), and close menu 90. To initiate display of the control menu options shown, the viewer may select a button on a remote control, look at a particular region of the screen, or even look at a particular region off the screen, such as the enable control menu region 92 located above the display in the example shown. When the load on-screen control menu control is selected, the menu items 80-90 may then overlay the current display content (such as a TV show). If the on-screen menu control elements are located near the periphery of the display (sides and top), deselecting (hiding) the onscreen menu may be achieved by simply returning the gaze to the center of the screen and resuming watching the displayed content. After a certain length of time in which no control elements are selected, the onscreen menu may fade and disappear.

When the subject 12 looks at a point on the display 14 that is within a control element region such as one associated with channel up 80 shown in FIG. 6, the control element may be selected. Feedback on which control element was selected may be provided to the user, such as by highlighting 94 the control element 80-90 with a color change, change of shape, etc. The control element may be defined by a geometric region on the screen. For example a rectangle, circle, or general polygon, or 3D volume if tracking in real world or 3D displays, although any shape may be used. To determine if a control element is being targeted, the POG 16 on the display 14 can be tested to see if it the POG 16 is within the control element region. While control elements may be shown with a specific size to the viewer, the actual target size may be slightly larger to allow for slight inaccuracies in the eye tracking system. For example the control target area may be 10% larger than the control display area.

To determine if the point-of-gaze is within a rectangular control element region, the following test may be applied:

IF ($POG_x$>$CONTROL_{left}$) AND ($POG_x$<$CONTROL_{right}$) AND
($POG_y$>$CONTROL_{bottom}$) AND ($POG_y$<$CONTROL_{top}$)
THEN the POG is inside CONTROL rectangle, wherein "CONTROL" refers to the control element region, and "top", "bottom", "left", and "right" define the position and dimensions of the region.

For circular control elements, defined by a center point and a radius, the following test may be applied to determine if the POG 16 is within the circle:

IF (squareroot (($POG_x$−$CONTROL_{center\_x}$)^2+($POG_y$−$CONTROL_{center\_y}$)^2)<$CONTROL_{radius}$)
THEN POG is inside CONTROL circle, wherein "CONTROL" refers to the control element region, and "centre_x" and "centre_y" refer to the location of the centre of the region and "radius" refers to the radius of the circular region.

For control elements defined by general polygons, it can be appreciated that any suitable tests may be used, such as the well known ray casting and angle summation techniques.

Activation of the targeted control element may be made by pressing a single button on the hand held remote control. Hands-free dwell time activation may also be used where the control is activated by dwelling on the control element for a predefined period of time. With dwell time, the POG 16 may move out of the control element briefly, due to the natural jittery motion of the eyes. In such an event, the control element may remain selected to prevent resetting a dwell time counter. A countdown indicator such as an internal shrinking shape, proportional to the remaining time to activate the control, may also be provided as feedback to the subject 12. Tracking a subject's eye blinks is another technique that may be used for controlling activation of a control element. Additionally, the control elements may be made semitransparent to allow media content to continue to play behind the control elements.

Figure 7:
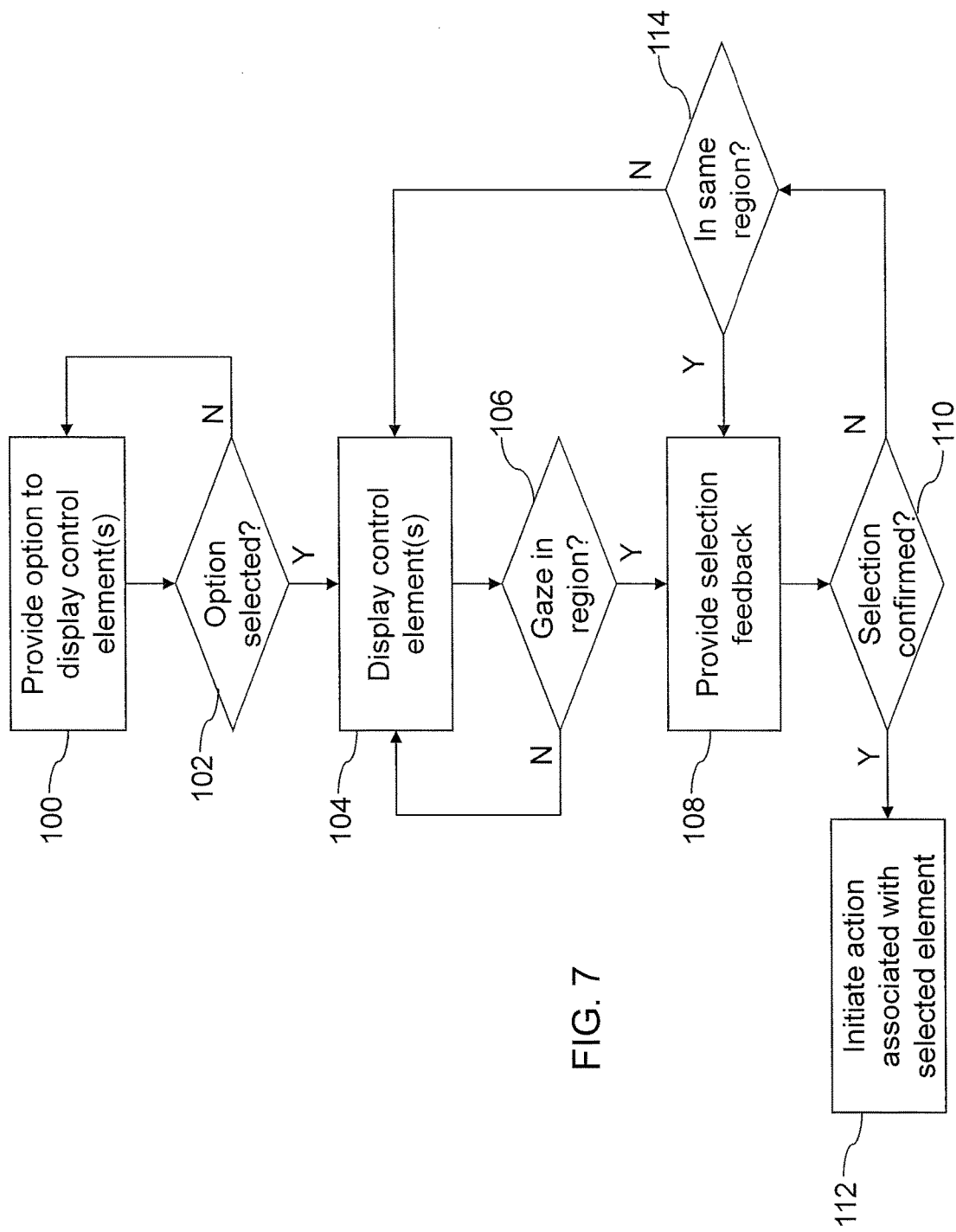
FIG. 7 is a flow chart illustrating an example set of operations that may be performed in enabling interactions with control elements on a display use eye gaze.

Turning now to FIG. 7, an example of a set of operations is shown that may be executed by the display 14, local processing system 22, media system 28, or any other system or module capable of displaying control elements on the display 14. At 100, an option is provided to display one or more control elements. As discussed above, this may be done in various ways, such as by enabling a menu to be invoked using a remote control or other peripheral device, or by gazing at an off-screen portion of the display 14, an on-screen control element, etc. The system or module being used may then determine at 102 whether or not the option has been selected. If not, control may return to 100. If the option has been selected, the one or more control elements may be displayed at 104. The system or module being used may then determine at 106 if a detected POG 16 is within a region associated with a displayed control element. If not, control may return to 104. Once the POG 16 is determined to be within a control element region, selection feedback may be provided at 108. For example, as discussed above, the control element may be highlighted, its color changed, etc.

After providing feedback indicating that the POG 16 is within a control element region, the system being used may then determine at 110 whether or not a selection of that control element has been confirmed. For example, an indication may be received from the gaze tracking system 20 of a fixation on the control element, a signal may be received from a remote control, etc. If a selection has been confirmed, the control system may initiate an action associated with the control element at 112, e.g., increase or decrease volume, adjust channel, etc. If a selection has not yet been confirmed at 110, the system being used may determine at 114 whether or not the POG 16 is still within the control element region. If so, the selection feedback may continue at 108. If the POG 16 is no longer within the control element region or a timer has expired or other criterion met, the selection feedback may be removed and normal display of the control elements resumed at 104.

Figure 8:
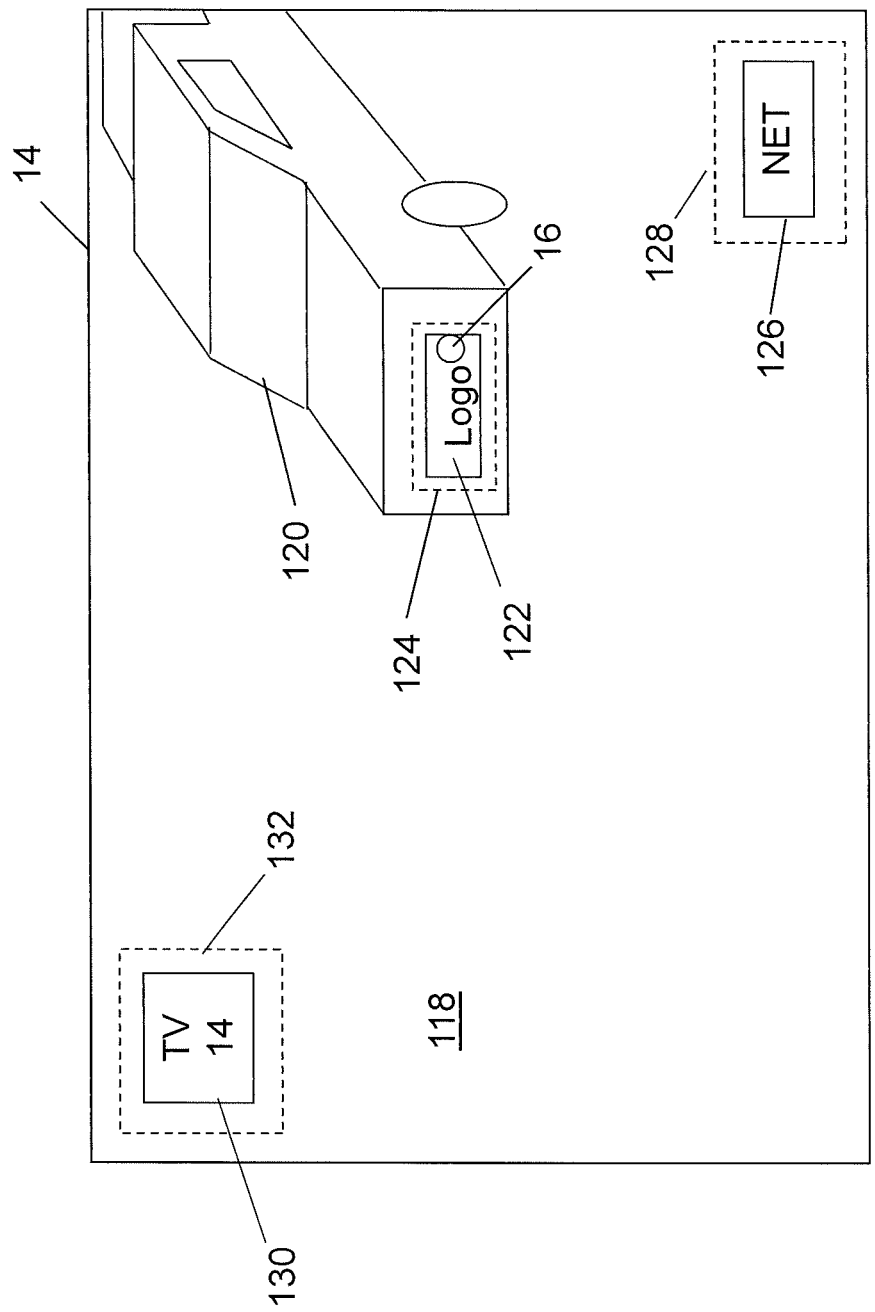
FIG. 8 is an example of a screen shot displaying media content.

FIG. 8 illustrates an example of a video frame of a scene 118 on a display 14. The video frame in this example has been processed to automatically identify content-of-interest regions. For example, the gaze tracking system 20 may provide the POG 16 corresponding to where on the display 14 the subject 12 was looking, which may then be linked to the content that was shown on the display 14. In the example shown in FIG. 8, the content-of-interest elements include a television viewer age recommendation warning 130, a name of a network 126 providing the content, and a product placement such as a vehicle logo 122 on the front of a vehicle 120 being shown in the scene 118. The respective regions of the screen occupied by these elements are determined manually or programmatically by outlining the corresponding content region. For example a first outline 132 outlines the warning 130, a second outline 128 outlines the network logo 126, and a third outline 124 outlines the vehicle logo 122. Programmatic detection of content may be done with pattern matching in an image. For example, a video sequence may be scanned for the occurrence of a corporate logo using scale and rotation invariant feature matching such as SIFT features [e.g., as discussed in Distinctive Image Features from Scale-Invariant Keypoints, David G. Lowe, International Journal of Computer Vision, January 2004].

The content-of-interest regions may be rectangles, ellipses, polygons or any other shape that surround the content-of-interest. For each video displayed, the content-of-interest regions may be defined by a sequence of 2D vertex points (e.g., ViX for the ith X coordinate, ViY for the ith Y coordinate and, for 3D systems, ViZ for the ith Z coordinate). The content-of-interest regions may also dynamically transform, translate, scale, and morph, to track the dynamic screen content. Key-frames which are smoothly interpolated in time to follow the video content on the display 14 can be used to allow for dynamic content-of-interest determinations. An example key frame list that defines a rectangle outlining the vehicle logo as the vehicle drives diagonally across the screen, starting at a video time of 5 minutes, 4 seconds and 230 millisecond; and lasting for 1 second, may appear as follows in Table 1:

TABLE 1

Example Key Frame List

| Timestamp | Content Name | V1X | V1X | V2X | V2Y | V3X | V3Y | V4X | V4Y |
|---|---|---|---|---|---|---|---|---|---|
| 00:05:04.230 | TruckLogo | 400 | 400 | 450 | 400 | 450 | 430 | 400 | 430 |
| 00:05:05:230 | TruckLogo | 300 | 300 | 350 | 300 | 350 | 330 | 300 | 330 |

The raw eye gaze data typically includes the X and Y coordinates on the screen where the user was looking at a particular time. The eye gaze data, when linked to the content-of-interest as described above, can be collected into a list indicating each content-of-interest region that was targeted by a POG 16. An example list of processed eye gaze data for the TruckLogo example above, where two fixations have hit the TruckLogo area of interest, may as follows in Table 2:

TABLE 2

Example List of Processed Eye Gaze Data

| User ID, | Content Name | Fixation ID | Start | Duration | X, | Y |
|---|---|---|---|---|---|---|
| 75248 | TruckBrand | 4282 | 00:05:04.500 | 0.550 | 425 | 420 |
| 75248 | TruckBrand | 4283 | 00:05:05.100 | 0.100 | 330 | 310 |

The content-of-interest region definitions may reside in the data collection and analysis system 24, or on the local processing system 22, and the analysis linking eye gaze data to content-of-interest regions can be performed at either location. If the analysis is performed on the local processing system 22, a resulting analysis file could be transmitted to the data collection and analysis system 24.

Figure 9:
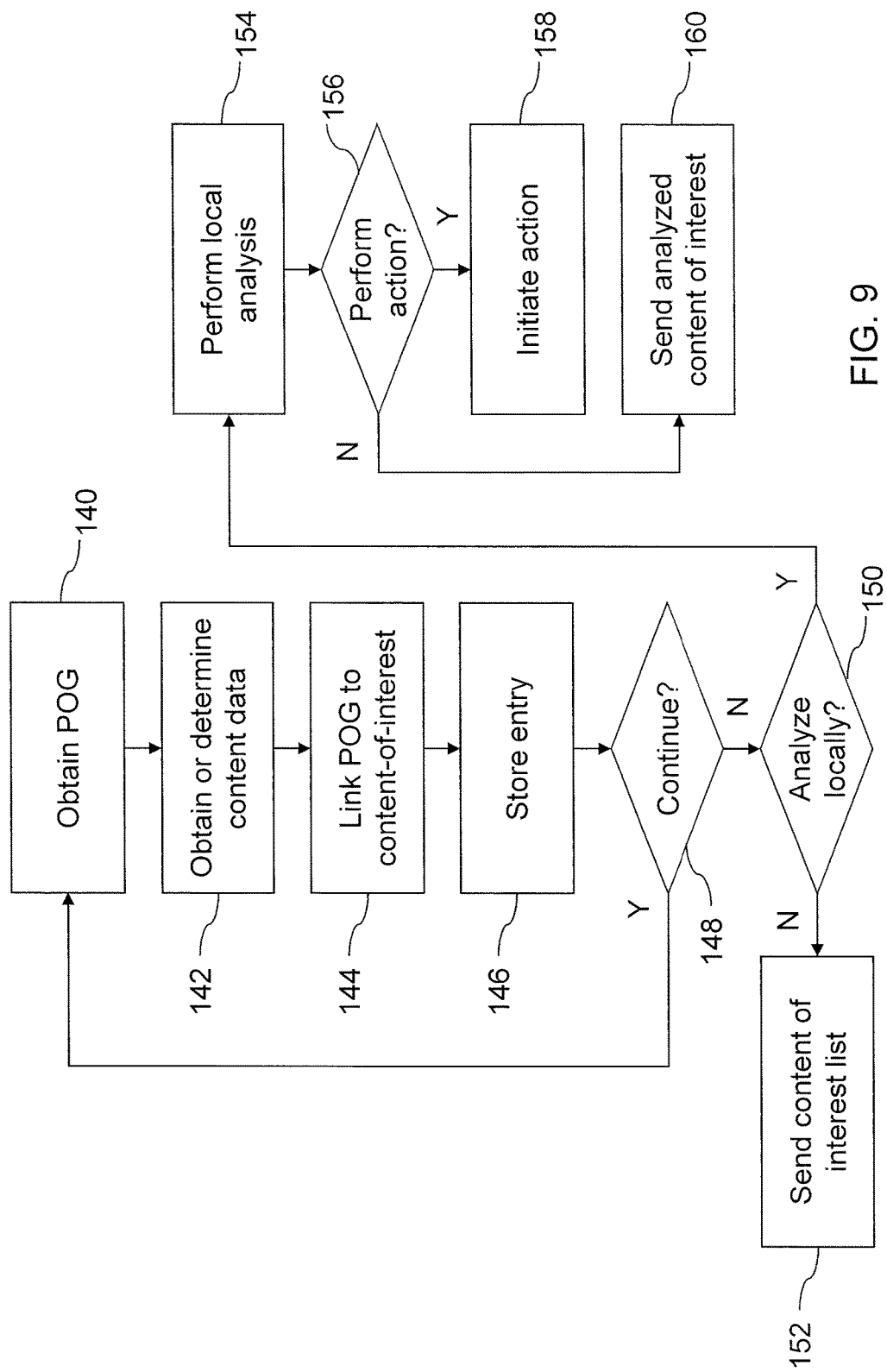
FIG. 9 is a flow chart illustrating an example set of operations that may be performed in analyzing media content according to eye gaze data.

Turning now to FIG. 9, an example of a set of operations is shown that may be executed by the local processing system 22, data collection and analysis system 24, media system 28, or any other system or module capable of linking POG 16 to content-of-interest and/or analyzing such data. At 140, the system performing the analysis obtains the POG 16. The POG 16 and/or related gaze data may be obtained directly from the gaze tracking system 20 or through the local processing system 22, e.g., if the analysis is being performed by the data collection and analysis system 24. Data indicative of the content-of-interest may be obtained or determined at 142. For example, the system being used may have information regarding what content is of interest or may determine content-of-interest from the media content itself. The POG 16 may then be linked to the content-of-interest at 144 and an entry stored at 146. The system being used then determines if content-of-interest is to still be analyzed at 148. For example, if the content-of-interest is moving through the display 14, the system may track that content-of-interest while it is on the display 14. Once the entry or entries associated with the content-of-interest have been obtained, the system determines whether or not to analyze locally at 150. If not, the content-of-interest list may be sent at 152, e.g., to the data collection and analysis system 24. If the content-of-interest is to be at least partially analyzed locally, a local analysis is performed at 154 and the system determines at 156 whether or not an action is to be performed. For example, determining that the subject 12 is focusing on a particular element may initiate the display of an advertisement, a modification of the focus, etc. If an action is to be performed, such an action is initiated at 158. If no action is to be performed, the analyzed or partially analyzed content-of-interest may be sent at 160, e.g., to the data collection and analysis system 24 for further processing and/or analysis.

Figure 10:
FIG. 10 is an example screen shot displaying an augmented reality (AR) layer on a scene including control elements and information associated with elements in the scene.

The techniques discussed above for interacting with 2D displays can also be extended to more complex displays 14 such as those providing virtual and augmented realities. In FIG. 10, an automotive heads up display (HUD) view 170 is shown. In the view 170 shown in FIG. 10 are a variety of information and interaction elements, which may be built into a windscreen, projected onto a windscreen, laser drawn, or shown through head mounted HUD glasses, or using any other suitable display technique. In such an environment 10, the gaze tracking system 20 may be head mounted, integrated into the automotive dash for nonintrusive tracking, etc. In such a system, the driver no longer needs to remove their eyes from the road to see information such as how fast they are going 172, and what channel the stereo is on 186. Smart sensors, such as sonar, radar, machine vision, as well as integration with sensors in the surrounding environment can be used to tag external vehicles with relative velocities 178, 180, remaining duration 182 of traffic lights and so forth.

Interaction with devices may not be safe or legal when the subject 12 (driver) needs to use their hands. By projecting on-screen elements as shown in FIG. 10, the elements may be interacted with using eye gaze as described above. For example, a cruise control setting 172 may be increased or decreased by looking at the plus (+) and minus (−) control boxes 174, 176. Likewise, a stereo channel 186 may be controlled by looking at on screen channel controls 184, 188. It is also possible to sound an alarm if the viewer is not looking at an appropriate display feature, such as a car that is braking quickly or a pedestrian walking in front of the vehicle. If the POG 16 does not intersect with the car or pedestrian a warning may sound and the onscreen overlay flashed.

The onscreen overlays may by their nature be drawn in front of other objects visible through the windshield. In this case using 3D eye tracking provides a means for determining at what depth that driver is currently viewing. For example, looking at on-screen elements will have a closer vergence angle between the left and right eye, than looking at objects in the distance in which the line of sight of the left and right eyes become increasingly parallel.

As with the TV display 14 shown in FIG. 6, the onscreen controls and information may be hidden to prevent obstruction of the view until otherwise selected. For example, gazing in a particular region of the display may bring up the stereo controls, or using voice commands such as 'Speed' may bring up an overlay showing the relative velocity of the current vehicle being looked at.

Figure 11:
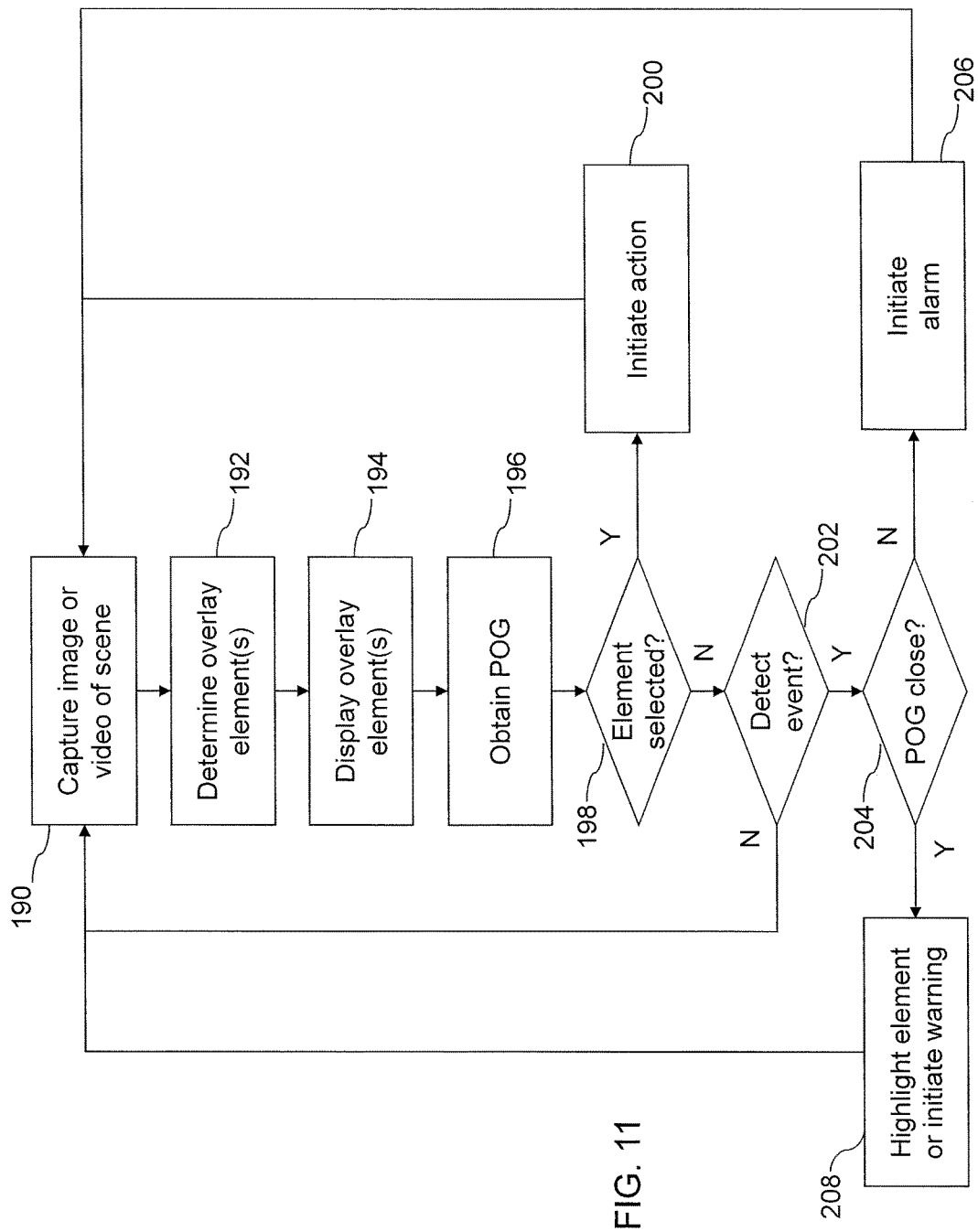
FIG. 11 is a flow chart illustrating an example set of operations that may be performed in displaying an AR layer on a scene.

Turning now to FIG. 11, an example of a set of operations is shown that may be executed by the local processing system 22, data collection and analysis system 24, media system 28, or any other system or module capable of having HUD elements projected onto a display 14. In such an example, it can be appreciated that the display 14 may correspond to a real-life image or scene as seen through HUD glasses, a windscreen, etc. At 190, the system being used captures an image or video of a scene. For example, a media system 28 in a vehicle may be used to obtain a video of the road as seen by the driver. The overlay elements to be displayed for the subject 12 are determined at 192 and displayed for the subject at 194. For example, using the video obtained at 190, the system being used may determine other vehicles in the scene 170 and identify the vehicles as content-of-interest to be tagged with relative speeds. The relative speeds may be determined using external sensors and associated with the vehicles in the scene to tag them with corresponding overlay elements. The system being used also obtains the POG 196 of the subject 12 at 196.

As discussed above, the overlay elements may include both control elements and information. At 198, the system being used determines whether or not an overlay element has been selected. If so, the associated action may be initiated at 200 and control returns to 190. If not, the system determines at 202 whether or not an event has been detected. For example, the system may track objects that appear in the screen that are not in the subject's line of sight or otherwise far from their POG 16. If no event has been detected, control may return to 190. If an event is detected, the system may then determine whether the POG 16 is relatively close to the object that has caused the event, which indicates whether or not the subject 12 has or will see the object, e.g., a rapidly braking car, pedestrian, etc. If the POG 16 is not close to the object causing the event, an alarm may be initiated at 206 to try to raise the subject's awareness and control may return to 190. If the POG 16 is relatively close to the object causing the event, the system may still provide a warning at 208, e.g., by highlighting the object, flashing something on the overlay in association with the object, etc.

It has been found that, to date, gaze tracking has most commonly been used in constrained environments such as with a desktop PC. However, the display 14 upon which the subject's gaze is being tracked may take many shapes and forms, and be used in a variety of environments 10. Long-range eye tracking, wherein the display 14 is located at a relatively larger distance from the subject 12, may become increasingly more common as eye tracking becomes more consumer oriented thus entering, for example, the living room environment 10. Environments that are less constrained, such as a living room, theater or boardroom; can add additional complexity to the gaze tracking system 20.

Figure 12:
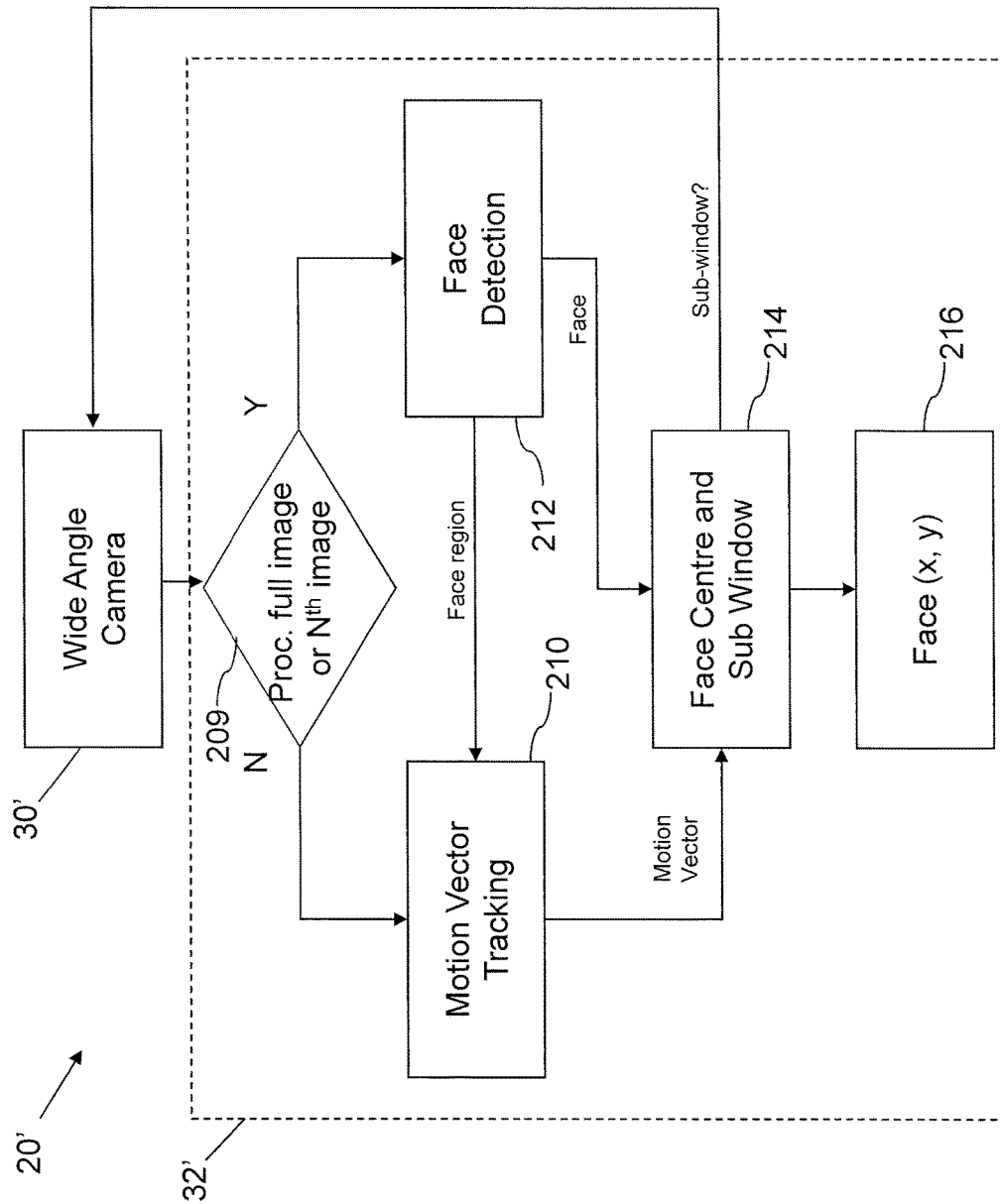
FIG. 12 is a flow chart illustrating an example set of operations that may be performed in gaze tracking on a display for long-range environments.

FIG. 12 illustrates a process that may be executed for performing eye gaze tracking on a display 14 in a long range environment 10 such as a living room, office, theatre, etc. Gaze tracking systems 20 such as that shown in FIGS. 1 and 2 use imaging devices 30 to image the face and eyes of a subject 12 remotely, in order to provide a "contactless" experience. In a long-range environment 10, the subject 12 is typically free to move about the environment 10 and the imaging device 30 would still need to capture the subject's eyes regardless of the subject's position within the environment 10. The gaze tracking system 20 would also need to capture images of the face and eyes of a subject 12 with enough spatial resolution to extract the image features needed for POG estimation. To do so, a fixed wide-angle camera 30' may be used to image the scene, identify the position of the subject 12, and direct the orientation of a narrow angle camera used for eye tracking.

To accomplish the above, a face detection algorithm may be used, e.g., the well-known algorithm for tracking Haar features [Paul Viola and Michael Jones: Robust Real-time Object Detection, Second International Workshop on Statistical and Computational Theories of Vision—Modeling, Learning, Computing, and Sampling, Vancouver, Canada, Jul. 13, 2001], to find the subject's face in the image from the wide angle camera 30'. Originally the entire image is processed 209, to identify the position of the face in the image, and a face region sub-image 222 around the face to speed up subsequent iterations of the face tracking algorithm. A grid of points is selected on the image of the subject's face which are then tracked with a motion flow algorithm at 210 to generate a face motion vector, using well-known optical flow algorithms such as tracking corner features or textures. The center of the face is tracked using the motion flow vectors 210 for N-1 iterations as they are fast to use, while the face detection 212 is used every N iterations which resets the motion flow points to prevent accumulation of motion errors. For example, for a 30 Hz camera, the motion flow tracking at 210 may operate 28 times a second (N=15), while the face tracking at 212 runs at a lower rate of 2 Hz. The average of the motion flow points are used to find the center of the face at 214, and determine the center face position (x, y) in pixels in the image at 216.

It can be appreciated that in the event that the face is lost in the sub image area of interest, the algorithm can reverts back to processing the full wide-angle image until the next face is detected. The process shown in FIG. 12 may be applied to any number of faces in the wide-angle scene to direct any number of narrow angle cameras (not shown). Faces in the wide-angle scene may be differentiated using facial recognition or biometric signals such as body size, height, etc. If a depth map 224 (see also FIG. 13) is available (lighter intensity shows closer regions while dark intensity shows farther regions), the depth information provides additional information for tracking the head position. For example the face is most likely to exist in the region that corresponds to the head on the human shape in the depth map.

Figure 13:
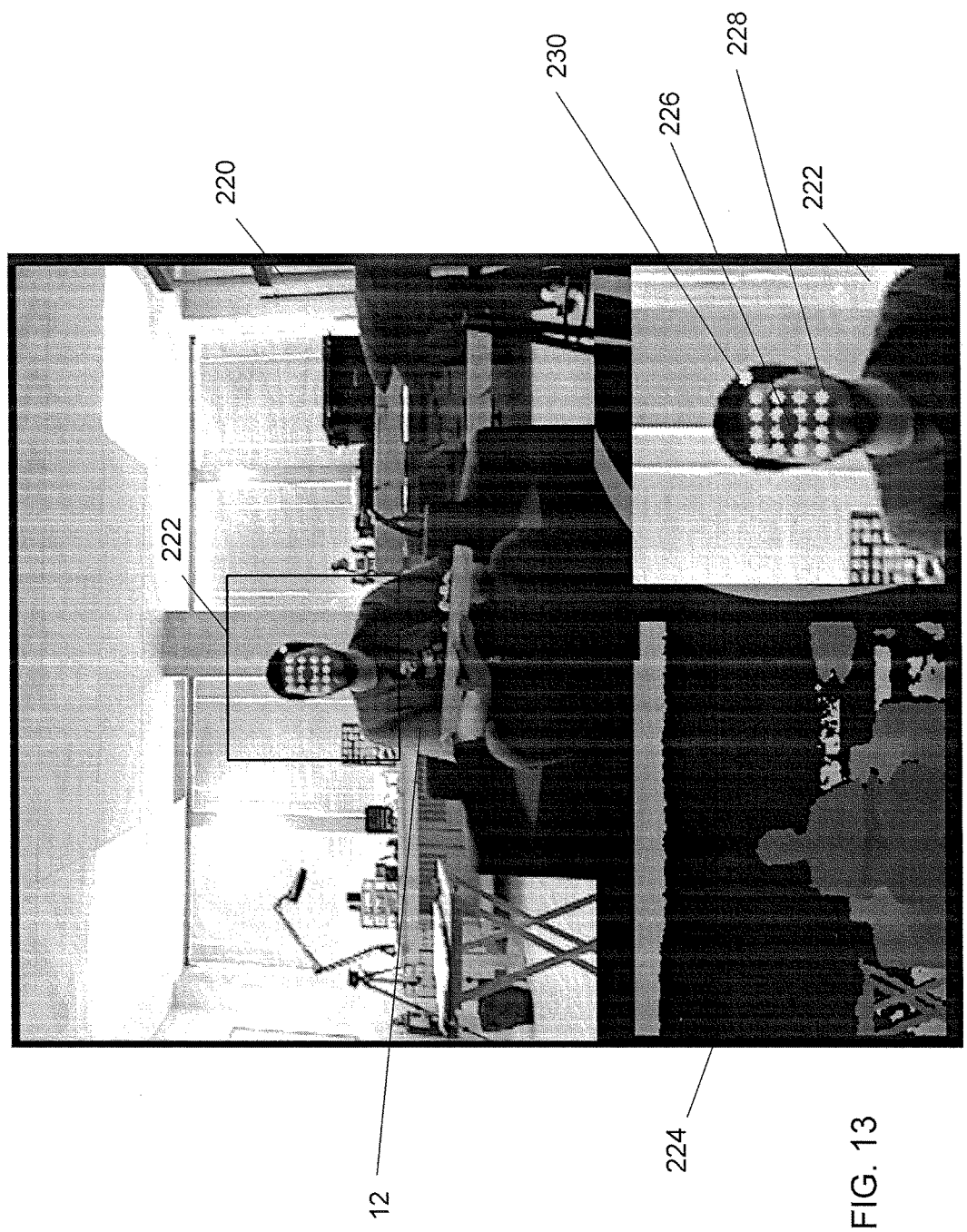
FIG. 13 is an example screen shot illustrating face tracking for a displayed scene.

FIG. 13 illustrates an example scene 220 of a relatively complex environment 10, wherein a subject 12 is seated on a couch watching TV. The face tracking algorithm in this example has detected a face and extracted a sub image 222 for the face area of interest. The center of the face 226 is identified with a large red circle, while the face motion vector points are identified with a 4×4 grid 228 of circles. The face tracking zero position 230 is shown as a circle adjacent the grid of circles, and is discussed further below.

Figure 14:
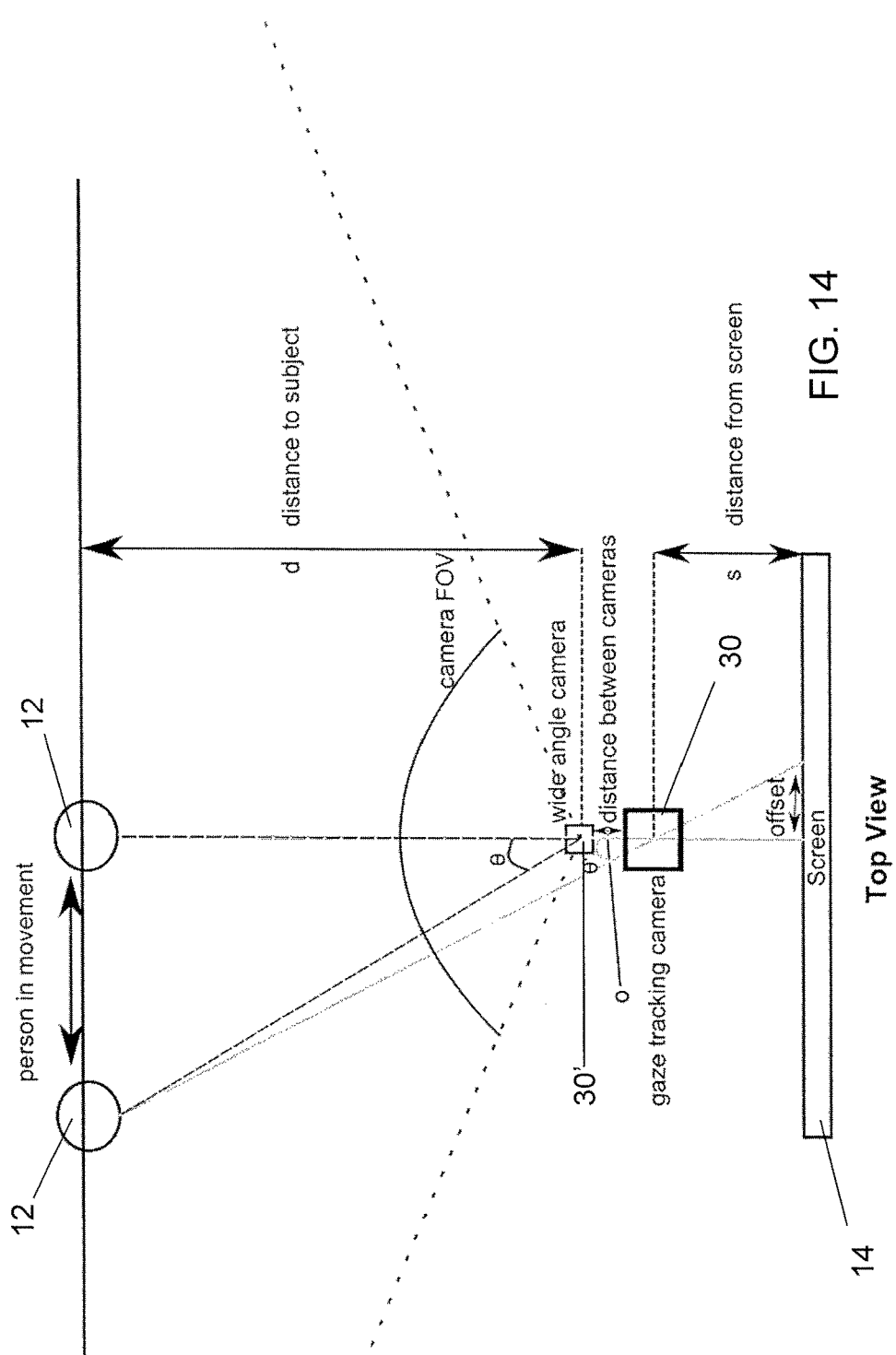
FIG. 14 is a schematic diagram illustrating point of gaze (POG) correction for long-range eye tracking.

FIG. 14 provides a schematic illustration of a POG correction technique for long-range gaze tracking. When the subject 12 moves with respect to the display 14 (screen in FIG. 14) and a pan/tilt system follows the subject 12, the POG accuracy degrades due to changing geometry. The accuracy degradation can be compensated for without user recalibration using correction factors based on the modified system geometry. The offset correction factor to apply to the point of gaze estimates in pixels is determined by finding the intersection of the subject's position, through the gaze tracking system 20, and onto the display 14. This provides a distance in X and Y (e.g., in meters) to correct for the offset between the POG 16 at the time of calibration and the current position. The offset may then be converted to pixels and applied to the POG 16.

Using the field of view angle of the wide angle camera 30', an angle θ can be found, which corresponds to the angle between the center of the subject's face in pixels in the WA image and a face 'zero' position. The face 'zero' is the position in the image where the face was first viewed by the system and the eye-tracker camera aligned to the face. Since the imaging device 30 may not be coincident with the wide angle camera 30', the field of view angles may not correspond between the imaging devices 30 and 30' directly.

Using trigonometry, and knowing the distance between the wide angle camera 30' and the subject 12, and the distance between the two imaging devices 30, 30' the subject's movement can be projected onto the display 14 and the degree of offset required to compensate for the movement determined.

The function to compute the angle offset can be performed as follow (making reference to FIG. 14):

d=distance from WA camera to viewer (a constant or measured at run-time with a depth tracker)

s=distance from gaze tracker to screen (a constant, measured once)

o=distance between cameras (a constant, measured once)

θ=the angle between the person and the WA camera

θ' =the angle between the person and the eye tracker

The angle of the viewer with respect to the eye tracker is determined as:

$$\tan \theta * d = \tan \theta' * (d+o)$$

$$\theta' = \arctan\left(\frac{\tan\theta}{1 + \frac{o}{d}}\right)$$

The correction offset in meters may then be computed as:

$$\text{offset}_m = s \tan(\theta').$$

The offset in units of meters may then be converted to pixels using the ratio of the display's resolution to physical display size:

$$\text{offset}_{pixel} = \text{offset}_m * \left(\frac{screen_{pixel}}{screen_m}\right)$$

The POG 16 is then corrected by applying the offset in pixels.

When the subject 12 is moving vertically (such as standing up or sitting down on a couch or chair) the same algorithm can apply vertically (to the Y axis offset) in a manner similar to how it can be applied horizontally (X axis offset).

If the face center 226 in the wide angle image is to the right of the face tracking zero position 230, the horizontal offset is added to the POG 16 X-coordinate while if the face 226 is to the left of the face tracking zero position 230 the offset is subtracted from the POG 16 X-coordinate. If the face 226 is below (lower) than the face zero 230, the vertical offset is added to the POG 16 Y-coordinate, if the face is above (higher) the offset is subtracted from the POG 16 Y-coordinate.

In addition to compensating for changes in horizontal and vertical subject position, changes in viewer depth may also be compensated. Using depth sensing technologies, such as the Microsoft® Kinect, it may be possible to operate the environment 10 as discussed above, while the subject 12 is getting closer to or moving away from the components of the environment 10. Knowledge of the viewer's depth may be used to control the camera lens zoom and focus to ensure high-quality images of the viewer face. Depth corrections may also be applied to the point of gaze estimation algorithm.

Figure 15:
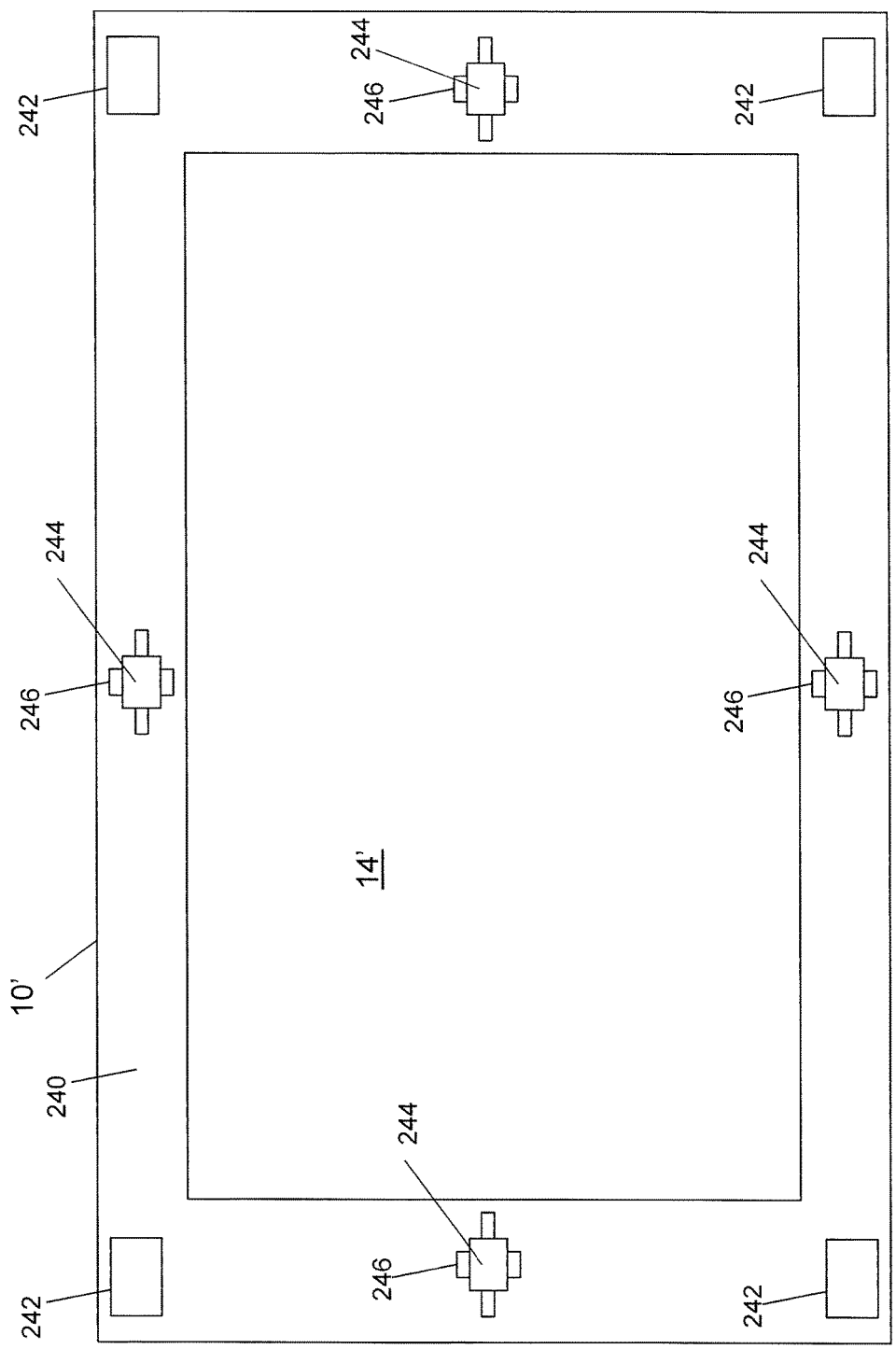
FIG. 15 is a plan view of a display with integrated eye tracking components.

It has also been found that, unlike desktop computing environments, mobile devices often integrate the use of touch into the user interface. Using a touch interface may result in obscuring cameras and/or lights used by the gaze tracking system 20, when the hands are interacting with the display 14. As shown in FIG. 15, placement of cameras 244 and lights 242, 246 on the mobile device 10' may reduce this problem. To overcome issues with gaze tracking cameras 244 being obscured, multiple cameras 244 and lights 242, 246 may be used as shown in FIGS. 15 and 16. The cameras 244 and lights 242, 246 may be located along each side of the mobile device 10', and while one potential placement is shown in FIGS. 15 and 16, any number of alternate positions are possible, such as locating the cameras 244 in the corners of the housing, and the lights 242, 246 around the edge of the mobile device 10'. As can be appreciated from FIG. 16, by providing multiple gaze tracking cameras 244, if one is obscured when the subject 12 interacts with the touch-sensitive display 14, the other cameras 244 are available to compensate.

Figure 17:
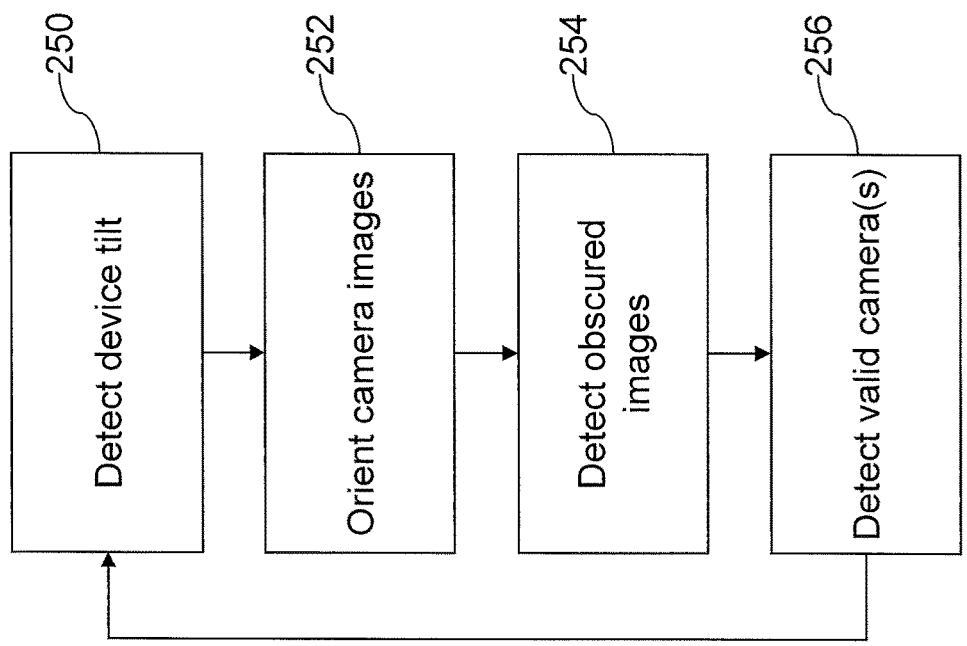

Mobile devices 10' are also typically handheld and allow for rotation of the device from portrait to landscape. To allow for this rotation the multiple cameras 244 and lights 242, 246 can be independently selected and the camera images rotated during operation of the gaze tracking system 20. As shown in FIG. 17, the device 10' may possess an accelerometer or some form of tilt sensing device which can be used to detect device tilt at 250 and to orient the camera images at 252 such that the viewer is always captured appropriately (i.e. with eyes horizontal in the image). Obscured images that do not show a properly formed face and eyes (e.g., where the camera 244 is obscured by the subject's hand and arm as shown in FIG. 16) may be detects at 254 and discarded for so that images from valid cameras 244 can be detected at 256 to obtain images that can be used in the subsequent gaze tracking process.

Figure 18:
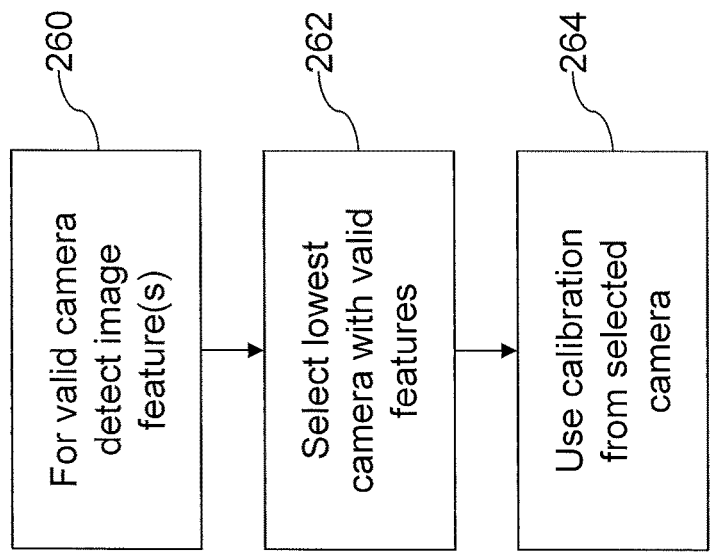
FIGS. 17 and 18 are flow charts illustrating an example set of operations that may be performed in performing eye tracking on a mobile device.

Turning now to FIG. 18, after valid cameras are detected at 256, the image features required for point of gaze estimation are identified (pupil and glints) at 260, and the camera 244 on the device 10' that has the lowest location is selected at 262 to be used for gaze tracking. It may be noted that the lowest camera (e.g., closest to the bottom of the display 14) may particularly advantageous, as such a camera 244 typically provides a better view of the eyes without the eyes being obscured by the eyelids.

During eye tracker calibration, all cameras calibrate at the same time. When the final eye tracker camera 244 is determined for use at 262, the appropriate calibration for that unit is used at 264, to determine the POG 16 on the display 14.

Techniques may be employed to reduce the power required for operation on a mobile, or battery-powered device. The LED's 242, 246 are only required while the shutter of the camera 244 lens is open and the camera 244 sensor capturing light. It is therefore possible to pulse the LED's on at higher power while the camera shutter is open, and turn the LED's off when the camera shutter is closed. It is desirable to operate the camera with a short exposure time which will require less power as the system lights are off for a greater percentage of the operating time. A short exposure time has the additional benefit of reducing the amount of smear, or motion blur, during exposure due to motion caused by holding the device in the operator's hand. Processing power may also be reduced by using a hardware region of interest with the camera, in which only the portion of the sensor that is imaging the eyes is transmit to the central processing unit. The remainder of the image, such as the rest of the face and background scene are ignored. This will reduce the amount of image processing needed, as well as bandwidth required to transmit image information from the camera to the processor.

It will be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the display 14, gaze tracking system 20, local processing system 22, data collection and analysis system 24, media system 28, and any component of or related to, or accessible or connectable thereto. Any application or module herein described may be implemented using computer readable/executable instructions that may be stored or otherwise held by such computer readable media.

The steps or operations in the flow charts and diagrams described herein are just for example. There may be many variations to these steps or operations without departing from the principles discussed above. For instance, the steps may be performed in a differing order, or steps may be added, deleted, or modified.

Although the above principles have been described with reference to certain specific examples, various modifications thereof will be apparent to those skilled in the art as outlined in the appended claims.

The invention claimed is:

1. A method of interacting with media content using gaze information, the method comprising having a system comprising a processor executing instructions in memory to perform the following steps:

displaying media content on a display device in an environment;

detecting an interaction with a set of selectable elements content from a control input via a control interface, wherein the control input is used to initiate interactions with the media content being displayed;

modifying the media content such that the set of selectable elements of the media content is made visible;

obtaining gaze information obtained by a gaze tracking system, for at least one subject viewing the media content on the display device, from a secondary device that is separate from the control interface;

determining from the gaze information that the subject's gaze is associated with a desired one of the one or more selectable elements now displayed, and providing feedback to the subject when such an association is determined;

detecting selection of the desired one of the one or more selectable elements from the control input via the control interface, while the subject's gaze is associated with the desired one of the one or more selectable elements now being displayed to confirm the selection of that selectable element;

modifying the media content to hide the set of selectable elements; and performing an action according to the selection of the desired one of the selectable elements, wherein the action executes a feature associated with the display.

2. The method of claim 1, wherein the action controls a feature of the display.

3. The method of claim 1, wherein the gaze information is indicative of a point of gaze.

4. The method of claim 1, the display providing a three dimensional (3D) output, the gaze information providing a 3D point of gaze.

5. A non-transitory computer readable storage medium comprising computer executable instructions for interacting with media content using gaze information, including instructions for:

displaying media content on a display device in an environment;

detecting an interaction with a set of selectable elements of the media content from a control input via a control interface, wherein the control input is used to initiate interactions with the media content being displayed;

modifying the media content such that the set of selectable elements of the media content is made visible;

obtaining gaze information obtained by a gaze tracking system, for at least one subject viewing the media content on the display device, from a secondary device that is separate from the control interface;

determining from the gaze information that the subject's gaze is associated with a desired one of the one or more selectable elements now displayed, and providing feedback to the subject when such an association is determined;

detecting selection of the desired one of the one or more selectable elements from the control input via the control interface, while the subject's gaze is associated with the desired one of the one or more selectable elements now being displayed to confirm the selection of that selectable element;

modifying the media content to hide the set of selectable elements; and performing an action according to the selection of the desired one of the selectable elements, wherein the action executes a feature associated with the display.

6. The computer readable storage medium of claim 5, the action controlling a feature of the display.

7. The computer readable storage medium of claim 5, wherein the gaze information is indicative of a point of gaze.

8. The computer readable storage medium of claim 5, the display providing a three dimensional (3D) output, the gaze information providing a 3D point of gaze.

9. A system comprising a processor and memory, the memory comprising computer executable instructions for interacting with media content using gaze information, that when executed by the processor cause the system to:

display media content on a display device in an environment;

detect an interaction with a set of selectable elements of the media content from a control input via a control interface, wherein the control input is used to initiate interactions with the media content being displayed;

modify the media content such that the set of selectable elements of the media content is made visible;

obtain gaze information obtained by a gaze tracking system, for at least one subject viewing the media content on the display device, from a secondary device that is separate from the control interface;

determine from the gaze information that the subject's gaze is associated with a desired one of the one or more selectable elements now displayed, and providing feedback to the subject when such an association is determined;

detect selection of the desired one of the one or more selectable elements from the control input via the control interface, while the subject's gaze is associated with the desired one of the one or more selectable elements now being displayed to confirm the selection of that selectable element;

modify the media content to hide the set of selectable elements; and perform an action according to the selection of the desired one of the selectable elements, wherein the action executes a feature associated with the display.

10. The system of claim 9, wherein the action controls a feature of the display.

11. The system of claim 9, wherein the gaze information is indicative of a point of gaze.

12. The system of claim 9, the display providing a three dimensional (3D) output, the gaze information providing a 3D point of gaze.

13. A method of detecting associations between gaze and content of interest and determining statistical information for such content of interest, the method comprising having a system comprising a processor executing instructions in memory to perform the following steps:

displaying media content to the at least one subject on a display device;

while displaying the media content, obtaining gaze information obtained by a gaze tracking system, for the at least one subject;

determining from the gaze information that a subject's gaze is associated with one or more portions of the media content being displayed, the one or more portions of media content corresponding to content of interest;

computing statistical information for each viewed content of interest, the statistical information comprising one or more of: time to first view, total time viewed, and number of repeated views; and outputting: i) the detected associations between the one or more subject's gaze and the content of interest, and ii) the corresponding statistical information;

wherein the content of interest comprises at least one of: a position and dimension associated with the content of interest in the media content, a time at which the content of interest is placed within the media content, and one or more tags or classifications defining the content of interest.

14. The method of claim 13, wherein associating the gaze information with the content of interest comprises obtaining demographic data for the at least one subject viewing the media content.

15. The method of claim 13, further comprising sending at least one of the gaze information and the associated content of interest to a data repository.

16. The method of claim 15, the data repository being located remote from the environment.

17. The method of claim 13, wherein the content of interest is detected automatically using pattern matching.

18. The method of claim 13, the gaze information being associated with multiple subjects viewing the same media content.

19. The method of claim 18, the multiple subjects being in a same location.

20. The method of claim 18, the multiple subjects being in a plurality of locations.

21. The method of claim 13, further comprising rating each media content in a media content database, based on the content of interest that media content contains relative to the computed statistical information on to which the at least one subject associates their gaze.

22. The method of claim 13, wherein the gaze information is indicative of a point of gaze.

23. The method of claim 13, the display providing a three dimensional (3D) output, the gaze information providing a 3D point of gaze.

24. A non-transitory computer readable storage medium comprising computer executable instructions for detecting associations between gaze and content of interest and determining statistical information for such content of interest, comprising instructions for:
displaying media content to the at least one subject on a display device;
while displaying the media content, obtaining gaze information obtained by a gaze tracking system, for the at least one subject;
determining from the gaze information that a subject's gaze is associated with one or more portions of the media content being displayed, the one or more portions of media content corresponding to content of interest;
computing statistical information for each viewed content of interest, the statistical information comprising one or more of: time to first view, total time viewed, and number of repeated views; and
outputting: i) the detected associations between the one or more subject's gaze and the content of interest, and ii) the corresponding statistical information;
wherein the content of interest comprises at least one of: a position and dimension associated with the content of interest in the media content, a time at which the content of interest is placed within the media content, and one or more tags or classifications defining the content of interest.

25. The computer readable storage medium of claim 24, wherein associating the gaze information with the content of interest comprises obtaining demographic data for the at least one subject viewing the media content.

26. The computer readable storage medium of claim 24, further comprising sending at least one of the gaze information and the associated content of interest to a data repository.

27. The computer readable storage medium of claim 26, the data repository being located remote from the environment.

28. The computer readable storage medium of claim 24, wherein the content of interest is detected automatically using pattern matching.

29. The computer readable storage medium of claim 24, the gaze information being associated with multiple subjects viewing the same media content.

30. The computer readable storage medium of claim 29, the multiple subjects being in a same location.

31. The computer readable storage medium of claim 29, the multiple subjects being in a plurality of locations.

32. The computer readable storage medium of claim 24, further comprising instructions for rating each media content in a media content database, based on the content of interest that media content contains relative to the computed statistical information on to which the at least one subject associates their gaze.

33. The computer readable storage medium of claim 24, wherein the gaze information is indicative of a point of gaze.

34. The computer readable storage medium of claim 24, the display providing a three dimensional (3D) output, the gaze information providing a 3D point of gaze.

35. A system comprising a processor and memory, the memory comprising computer executable instructions for detecting associations between gaze and content of interest and determining statistical information for such content of interest, that when executed by the processor cause the system to:
display media content to the at least one subject on a display device;
while displaying the media content, obtain gaze information obtained by a gaze tracking system, for the at least one subject;
determine from the gaze information that a subject's gaze is associated with one or more portions of the media content being displayed, the one or more portions of media content corresponding to content of interest;
compute statistical information for each viewed content of interest, the statistical information comprising one or more of: time to first view, total time viewed, and number of repeated views; and
output: i) the detected associations between the one or more subject's gaze and the content of interest, and ii) the corresponding statistical information;
wherein the content of interest comprises at least one of: a position and dimension associated with the content of interest in the media content, a time at which the content of interest is placed within the media content, and one or more tags or classifications defining the content of interest.

36. The system of claim 35, wherein associating the gaze information with the content of interest comprises obtaining demographic data for the at least one subject viewing the media content.

37. The system of claim 35, wherein the content of interest is detected automatically using pattern matching.

38. The system of claim 35, the gaze information being associated with multiple subjects viewing the same media content.

39. The system of claim 38, the multiple subjects being in a same location.

40. The system of claim 38, the multiple subjects being in a plurality of locations.

41. The system of claim 35, further configured to rate each media content in a media content database, based on the content of interest that media content contains relative to the computed statistical information on to which the at least one subject associates their gaze.

42. The system of claim 35, wherein the gaze information is indicative of a point of gaze.

43. The system of claim 35, the display providing a three dimensional (3D) output, the gaze information providing a 3D point of gaze.

44. The system of claim 35, further configured to send at least one of the gaze information and the associated content of interest to a data repository.

45. The system of claim 44, the data repository being located remote from the environment.

* * * * *

UNITED STATES PATENT AND TRADEMARK OFFICE
CERTIFICATE OF CORRECTION

PATENT NO. : 10,182,720 B2  
APPLICATION NO. : 13/870888  
DATED : January 22, 2019  
INVENTOR(S) : Craig A. Hennessey and Jacob Fiset Page 1 of 1

It is certified that error appears in the above-identified patent and that said Letters Patent is hereby corrected as shown below:

In the Claims

In Claim 1, Line 47 of Column 16, add "of the media" immediately after "selectable elements".

Signed and Sealed this
Twenty-sixth Day of March, 2019

Andrei Iancu
*Director of the United States Patent and Trademark Office*